US012409155B1

(12) United States Patent
Leeah et al.

(10) Patent No.: US 12,409,155 B1
(45) Date of Patent: Sep. 9, 2025

(54) READY TO USE LET FORMULATIONS

(71) Applicant: QuVa Pharma, Inc., Sugar Land, TX (US)

(72) Inventors: Travis A. Leeah, Sugar Land, TX (US); Jianping Chen, Sugar Land, TX (US)

(73) Assignee: QuVa Pharma Inc., Sugar Land, TX (US)

( * ) Notice: Subject to any disclaimer, the term of this patent is extended or adjusted under 35 U.S.C. 154(b) by 0 days.

(21) Appl. No.: 17/685,792

(22) Filed: Mar. 3, 2022

Related U.S. Application Data

(60) Provisional application No. 63/162,593, filed on Mar. 18, 2021.

(51) Int. Cl.
| | | |
|---|---|---|
| A61K 31/167 | (2006.01) | |
| A61K 9/06 | (2006.01) | |
| A61K 31/137 | (2006.01) | |
| A61K 31/245 | (2006.01) | |

(52) U.S. Cl.
CPC .............. *A61K 31/167* (2013.01); *A61K 9/06* (2013.01); *A61K 31/137* (2013.01); *A61K 31/245* (2013.01)

(58) Field of Classification Search
CPC ...... A61K 31/167; A61K 9/06; A61K 31/137; A61K 31/245
USPC ....................................................... 514/536
See application file for complete search history.

(56) References Cited

U.S. PATENT DOCUMENTS

| | | | |
|---|---|---|---|
| 5,585,398 A | 12/1996 | Ernst | |
| 6,708,822 B1 * | 3/2004 | Muni | A61K 31/196 206/568 |
| 8,628,805 B2 | 1/2014 | Bailie | |
| 10,952,962 B1 | 3/2021 | Leeah | |
| 10,952,963 B2 | 3/2021 | Leeah | |
| 2008/0131527 A1 * | 6/2008 | Sheil | A61L 26/008 424/722 |
| 2019/0314278 A1 * | 10/2019 | Leeah | A61P 29/02 |
| 2021/0251888 A1 | 8/2021 | Leeah | |

FOREIGN PATENT DOCUMENTS

WO    WO-2022016015 A1 *    1/2022    ........... A61K 31/137

OTHER PUBLICATIONS

Nationwide Children's LET Gel II , reviewed on Mar. 23, 2010,, https://www.sefh.es/fichadjuntos/LETGel.pdf, (Year: 2010).*
Blue Gel Anesthetic , DailyMed, updated on Feb. 22, 2021, https://dailymed.nlm.nih.gov/dailymed/drugInfo.cfm?setid=93c10d9e-aaa2-402c-a137-630a5f4eac88 (Year: 2021).*
Grubstein et al. Drug Dev. Ind. Pharm. (1992) 18(14): 1549-1566., "Stabilization of Epinephrine in a Local Anesthetic Injectable Solution using Reduced Levels of Sodium Metabisulfite and EDTA" (Year: 1992).*
Berge et al., Pharmaceutical Salts, Journal of Pharmaceutical Sciences (1977) 66(1), 1-19 ("Berge").
Bernards et al., Effect of Epinephrine on Lidocaine Clearance In Vivo, Anesthesiology (1999) 91(4): 962-968 ("Bernards").
Connick et al., Equilibrium Constant for the Dimerization of Bisulfite Ion to Form S2052-, Inorganic Chemistry (1982) 21(1): 103-107 ("Connick").
Connors et al., Chemical Stability of Pharmaceuticals: A Handbook for Pharmacists, 2nd Ed. (1986), pp. 438-448 "Connors").
Edge Pharma's LET (5%/0.05%/0.5%) Gel Topical Anesthetic, see edgepharma.com/products/nonsterile-products/, last accessed on Feb. 26, 2021.
Ernst et al. LAT (Lidocaine-Adrenaline-Tetracaine) Versus TAC (Tetracaine-Adrenaline-Cocaine) for Topical Anesthesia in Face and Scalp Lacerations, American Journal of Emergency Medicine (1995) 13(2): 151-154 ("Ernst 1995").
Fagron's LETS Gel Kit™ Convenience Pack (4%/0.1%/0.5%), us.fagron.com/sites/default/files/wysiwyg/faus_letsgelkit_instructions_0118_vfinal.pdf, last accessed on Feb. 26, 2021.
Fagron Inc. Issues Voluntary Nationwide Recall of LETS Gel Kit Convenience Packs Due to Potential Microbial Contamination of Non-Sterile Products, FDA Publish Date of Nov. 1, 2019, www.fda.gov/safety/recalls-market-withdrawals-safety-alerts/fagron-inc-issues-voluntary-nationwide-recall-lets-gel-kit-convenience-packs-due-potential-microbial, last accessed on Mar. 1, 2021 ("LETS Gel Kit™ Product Recall Notice").
Fagron's LET Sterile Topical Gel, www.fagronsterile.com/let-gel, last accessed on Mar. 2, 2021.
Flynn, G.L., Buffers—pH Control within Pharmaceutical Systems, Journal of the Parenteral Drug Association (1980) 34 (2) 139-162 ("Flynn").
Grubstein et al., Stabilization of Epinephrine in a Local Anesthetic Injectable Solution using Reduced Levels of Sodium Metabisulfite and EDTA, Drug Dev. Ind. Pharm. (1992) 18(14): 1549-1566.
Handbook of Pharmaceutical Excipients, 6th Ed., Eds. Rowe et al. (2009), pp. 181-183 247-250, 311-324, 438-441, 506-509 ("Handbook").
Kundu et al., Principles of Office Anesthesia: Part II. Topical Anesthesia, Am. Fam. Physician (2002) 66(1): 99-102 ("Kundu").
Larson et al., Stability of epinephrine hydrochloride in an extemporaneously compounded topical anesthetic solution of idocaine, racepinephrine, and tetracaine, American Journal Health-System Pharmacy (1996) 53(6): 659-662 ("Larson").
Lidocaine Jelly, Prescribing Information, as of Oct. 1, 2020.

(Continued)

*Primary Examiner* — Amy L Clark
*Assistant Examiner* — Liyuan Mou
(74) *Attorney, Agent, or Firm* — Merchant & Gould P.C.; Daniel R. Evans

(57) ABSTRACT

Disclosed herein is a pharmaceutical formulation comprising lidocaine, epinephrine, and tetracaine. Also disclosed herein is a process for preparing the pharmaceutical formulation comprising lidocaine, epinephrine, and tetracaine, as well as methods for using the pharmaceutical formulation.

8 Claims, No Drawings

(56) References Cited

OTHER PUBLICATIONS

The Merck Index: An Encyclopedia of Chemicals, Drugs, and Biologicals, 14th Edition (2006), pp. 3619, 5480, and 9191 ("Merck Index").
Nationwide Children's compounding report dated Mar. 23, 2010 related to LET II 3ML Topical Gel, www.nationwidechildrens.org/-/media/nch/specialties/pharmacy/compounding-formulas/let-gel.ashx, last accessed on Mar. 2, 2021.
Resch et al., Topical Anesthesia for Pediatric Lacerations: A Randomized Trial of Lidocaine-Epinephrine-Tetracaine Solution Versus Gel, Annals of Emergency Medicine (1998) 32(6): 693-697 ("Resch").
Sabatier et al., Simultaneous HPLC determination of lidocaine-epinephrine-tetracaine in a topical solution for pediatric anesthesia, Journal of Pharmacy Research (2016) 10(11): 692-695 ("Sabatier").
Sherman et al., Let Us Use LET: A Quality Improvement Initiative, Pediatric Emergency Care (2016) 32(7): 440-443 "Sherman").
Singer et al., LET versus EMLA for Pretreating Lacerations: A Randomized Trial, Academic Emergency Medicine (2001) 8(3): 223-230 ("Singer").
U.S. Pharmacopeia 28, (2005), pp. 3-12 and 2457-2460 ("USP 28").
U.S. Pharmacopeia 43 | National Formulary 38, Lidocaine, Racepinephrine, and Tetracaine Hydrochlorides Compounded Topical Gel, (2020), pp. 3—("USP 43").
Zanon et al., Stability of a novel Lidocaine, Adrenaline and Tetracaine sterile thermosensitive gel: A ready-to-use formulation, European Journal Pharmaceutical Sciences (2019) 136: 104962 (1-6), DOI: 10.1016/j.ejps.2019.104962 ("Zanon").
CAS SciFinder monograph for Edetate Disodium Anhydrous (CAS No. 139-33-3), 2025 (2 pp).
CAS SciFinder monograph for Na2EDTA DH (CAS No. 6381-92-6), 2025 (2 pp).
Dec. 13, 2019 Wayback capture of FDA Notice regarding single entity drug products, 3 pp.

\* cited by examiner

US 12,409,155 B1

READY TO USE LET FORMULATIONS

RELATED APPLICATION

This application claims priority to U.S. Provisional Patent Application No. 63/162,593, filed on Mar. 18, 2021.

FIELD OF THE INVENTION

Disclosed herein is a pharmaceutical formulation comprising lidocaine, epinephrine, and tetracaine. Also disclosed herein is a process for preparing the pharmaceutical formulation, as well as methods for using the pharmaceutical formulation.

BACKGROUND

Lidocaine and tetracaine are known local anesthetics, while epinephrine is vasoconstrictor. Merck Index. Epinephrine may be used in combination with a local anesthetic to prolong the duration of peripheral and central neuraxial blocks. Bernards at 962 and Kundu at 99.

In the mid-1990's, Ernst contemplated the combination of lidocaine, epinephrine, and tetracaine (aka LET or LAT) as a topical anesthetic for suturing lacerations. Ernst 1995. LET may be formulated as a topical solution or gel, each of which equally efficacious. Resch at 693.

Ernst 1996 discloses a LET topical solution including lidocaine (4%), epinephrine (0.05%), tetracaine (0.5%), benzyl alcohol (2% v/v), and water preserved with methyl paraben (0.05%) and propylparaben (0.025%). Ernst 1996 at column 7, lines 4-17. As a point of reference, percentages disclosed herein refer to percent mass-by-volume, unless specified otherwise. Ernst 1996 also discloses a LET topical gel included lidocaine (4%), epinephrine (0.05%), tetracaine (0.5%), hydroxyethyl cellulose (3%), and water preserved with methyl paraben (0.05%) and propylparaben (0.025%). Ernst 1996 at column 11, lines 13-28.

Ernst's LET products may be acceptable for immediate use but are unacceptable for long-term storage because epinephrine is known to undergo oxidative degradation in the presence of molecular oxygen, heavy metals, ultraviolet light, and increased pH. See Grubstein at 1550; see also Connors at 438-439 and Baillie. An antioxidant (e.g., bisulfite ($HSO_3^-$)) may be added to an epinephrine-containing composition to minimize oxygen-mediated oxidation, but epinephrine is also known to degrade by nucleophilic substitution with bisulfite. Connors at 439. Alternative antioxidants that may be used include, for example, sulfite ($SO_3^{2-}$) or metabisulfite ($S_2O_5^{2-}$), but these alternatives may also result in epinephrine degradation because each of bisulfite, sulfite, and metabisulfite may interconvert via pH-dependent equilibria. Id. at 441-442.

The stability of LET topical products has been the subject of numerous reports and monographs. See, e.g., Larson, Sabatier, and USP 43. For instance, a LET (4%/0.225%/0.5%) topical solution including sodium metabisulfite (0.063%) in an amber glass bottle reportedly has a stability of 4 weeks (at about 18° C.) and 26 weeks (at about 4° C.). See Larson at 659, 661. Larson's LET topical solution contains no preservative.

Additionally, a LET (4%/0.05%/0.5%) topical gel including sodium bisulfite (0.074%) stored in an amber plastic syringe reportedly has a shelf-life of 21 days (at about 25° C.) and 150 days (at about 4° C.). See LET II 3ML Topical Gel. The LET II 3ML Topical Gel includes methylparaben and propylparaben as preservatives.

An alternative LET (4%/0.1%/1%) gel product including sodium bisulfite (0.3%) stored in a light-resistant container reportedly has a beyond-use date of not more than 60 days when stored refrigerated or at room temperature. USP 43. The USP 43 LET topical gel includes methylparaben and propylparaben as preservatives. As a point of reference, USP 28 states that the beyond-use date (or "BUD") is the date after which a compounded preparation is not to be used and is determined from the date the preparation is compounded. USP 28<795> at 2458.

The aforementioned LET topical products may be compounded by a qualified pharmacist from commercially available materials. An alternative LET (4%/0.1%/0.5%) gel product includes all of the ingredients necessary to make a LET gel product including sodium metabisulfite (0.075%), with a reported beyond-use date of 90 days when stored in amber syringes. See LETS GEL KIT™ Convenience Pack; see also Muni at columns 17-18 related to FIRxST® (Unit Use of Compounding Kit) LAT. Interestingly, the LETS GEL KIT™ Convenience Pack contains no added preservative. The FDA recently reported a voluntary recall of the LETS GEL KIT™ Convenience Pack products due to potential microbial contamination. As LET topical products are used clinically to facilitate suturing of lacerations, it is of particular interest to provide a product with no microbial contaminants. Microbial contamination of a LET topical product may be minimized by use of a preservative, by ultrafiltration, or by steam sterilization. A LET product, which includes hydroxyethylcellulose, sterilized by steam may result a substantial loss of epinephrine. Zanon at 4.

A downside of the known LET topical products is reduced room temperature stability, and in certain instances, reduced antimicrobial effectiveness. The LET formulations disclosed herein address and overcome the problems of known LET topical products.

DETAILED DESCRIPTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The term "about" has its customary meaning. See, e.g., USP 28 at 7.

The terms "optional" or "optionally" as used herein means that a subsequently described event or circumstance may but need not occur, and that the description includes instances where the event or circumstance occurs and instances in which it does not.

The expression "epinephrine," as used herein refers to, for example, L-epinephrine or a combination of L-epinephrine and D-epinephrine, for example, racepinephrine.

The expression "sulfite," as used herein refers to metabisulfite ($S_2O_5^{2-}$), sulfurous acid ($H_2SO_3$), monobasic sulfite (viz., bisulfite ($HSO_3^-$)), dibasic sulfite ($SO_3^{2-}$), or a combination thereof. It may be appreciated that metabisulfite ($S_2O_5^{2-}$) hydrolyzes to form bisulfite ($HSO_3^-$) with an equilibrium constant of about 14. See Connors at 441-442; see also Connick at 103. Thus, use of metabisulfite ($S_2O_5^{2-}$) may result in the formation of two mole equivalents of monobasic bisulfite ($HSO_3^-$). It also may be appreciated that monobasic bisulfite ($HSO_3^-$) undergoes a pH-dependent equilibrium to form sulfurous acid ($H_2SO_3$) with a pKa of about 1.76 and dibasic sulfite ($SO_3^{2-}$) with a pKa of about 7.20. See Connors at 441-442. Monobasic bisulfite ($HSO_3^-$) may be the predominant sulfite species in solution at pH values from about 3.6 to about 4.0. Practically speaking, the expression "sulfite" refers to metabisulfite ($S_2O_5^{2-}$), monobasic sulfite (viz., bisulfite ($HSO_3^-$)), or a combination thereof. For instance, one may use a sodium salt of dibasic sulfite (e.g., $Na_2SO_3$) and adjust the solution to a pH value from about 3.6 to about 4.0 to obtain principally monobasic sulfite ($HSO_3^-$).

An aspect of the present disclosure relates to a pharmaceutical formulation, comprising: lidocaine or a pharmaceutically acceptable salt thereof, in an amount of about 30 mg/mL to about 50 mg/mL based on lidocaine free base; epinephrine or a pharmaceutically acceptable salt thereof, in an amount of about 0.25 mg/mL to about 2.5 mg/mL based on epinephrine free base; tetracaine or a pharmaceutically acceptable salt thereof, in amount of about 3 mg/mL to about 10 mg/mL based on tetracaine free base; a sulfite comprising metabisulfite ($S_2O_5^{2-}$), bisulfite ($HSO_3^-$), or a combination thereof, a chelating agent in an amount of from about 0.1 mg/mL to about 1 mg/mL; an antimicrobial effective amount of a preservative; optionally, a glycol, in an amount of about 1 mg/mL to about 20 mg/mL; optionally, a pharmaceutically acceptable buffer; optionally, a sufficient amount of a gelling agent; a sufficient amount of water; wherein the formulation has a pH of from about 3.6 to about 4.2; and wherein the formulation has a ratio of the mass amount (in mg) of epinephrine free base to the mole amount of sulfur in the sulfite (in mmol) that ranges from 179 to 185.

In one aspect, a pharmaceutical formulation disclosed herein comprises lidocaine or a pharmaceutically acceptable salt thereof, in an amount of about 30 mg/mL to about 50 mg/mL based on lidocaine free base, and all values in between, including, for example, about 35 mg/mL, about 40 mg/mL, and about 45 mg/mL.

In one aspect, a pharmaceutically acceptable salt of lidocaine includes, for example a hydrochloride salt (e.g., lidocaine hydrochloride), which may be present as an anhydrate or a hydrate (e.g., monohydrate). In another aspect, a pharmaceutically acceptable salt of epinephrine free base includes, e.g., a hydrochloride salt or a bitartrate salt (e.g., L-epinephrine bitartrate. racepinephrine hydrochloride, or racepinephrine bitartrate).

One may appreciate that a pharmaceutically acceptable salt of each of lidocaine, tetracaine, and epinephrine may be selected from known pharmaceutically acceptable salts. See, e.g., Berge.

The amount of epinephrine free base includes about 0.25 mg/mL to about 2.5 mg/mL and all values in between, for example, about 0.5 mg/mL, about 1 mg/mL, about 1.25 mg/mL, about 1.2 mg/mL, about 1.8 mg/mL, about 2 mg/mL, and about 2.25 mg/mL. In certain instances, it may be desirable to include a slight excess of epinephrine over that amount of the label claim. For instance, for a label claim of 0.5 mg/mL, it may be desirable to have an initial epinephrine amount of, for example, 0.51 mg/mL.

In certain aspects, the pharmaceutical formulation may comprise L-epinephrine free base in an amount of about 0.25 mg/mL. In other instances, the pharmaceutical formulation may comprise racepinephrine free base in an amount of about 0.5 mg/mL.

In one aspect, a pharmaceutical formulation disclosed herein comprises tetracaine or a pharmaceutically acceptable salt thereof, in an amount of about 3 mg/mL to about 10 mg/mL based on tetracaine free base, and all values in between, including, for example, about 3 mg/mL, about 4 mg/mL, about 5 mg/mL, about 6 mg/mL, about 7 mg/mL, about 8 mg/mL, and about 9 mg/mL.

In another aspect, a pharmaceutically acceptable salt of tetracaine includes, e.g., a hydrochloride salt (e.g., tetracaine hydrochloride).

LET formulations disclosed herein, include, for example, solutions or gels (regular or thick) having a lidocaine content of about 3% to about 5%, an epinephrine content of about 0.025% to about 0.25%, and a tetracaine content of about 0.3% to about 1% (viz., LET (3-5%/0.025-0.25%/0.3-1%) solution or gel). Specific LET formulations include LET (4%/0.05%/0.5%) gel, LET (4%/0.1%/0.5%) gel, LET (4%/0.18%/0.5%) gel, and LET (4%/0.225%/0.5%) solution.

In one aspect, the pharmaceutical formulation comprises a sulfite comprising metabisulfite ($S_2O_5^{2-}$), bisulfite ($HSO_3^-$), or a combination thereof. The sulfite may be present as a pharmaceutically acceptable salt, for example, sodium, potassium, and the like.

The amount of sulfite may depend on the amount of epinephrine. For example, the mmol amount of metabisulfite ($S_2O_5^{2-}$) may be determined by multiplying the mass (in mg) amount of epinephrine per mL by about 0.52 (e.g., 0.5194). Additionally, the mmole amount of bisulfite ($HSO_3^-$) may be determined by multiplying the mass (in mg) amount of epinephrine per mL by about 0.57 (e.g., 0.5686). In certain aspects, the sulfite may be derived from both metabisulfite and bisulfite with the understanding that the formulation has a ratio of the mass amount (in mg) of epinephrine free base to the mole amount of sulfur in the sulfite (in mmol) that ranges from 179 to 185, and all values in between, for example, 180, 181, 182, 183, and 184. In certain aspects, the formulation has a ratio of the mass amount (in mg) of epinephrine free base to the mole amount of sulfur in the sulfite (in mmol) of about 183.

In certain aspects, the pharmaceutical formulation may comprise a chelating agent in an amount of from about 0.1 mg/mL to about 1 mg/mL and all values in between, including, for example, about 0.2 mg/mL, about 0.3 mg/mL, about 0.4 mg/mL, about 0.5 mg/mL, about 0.6 mg/mL, about 0.7 mg/mL, about 0.8 mg/mL, and about 0.9 mg/mL.

Examples of chelating agents include, but are not limited to, one or more of disodium edetate, edetate calcium disodium, edetic acid, hydroxyethylethylenediaminetriacetic acid, pentetic acid, sodium edetate, trisodium edetate, and the like.

One may appreciate that disodium EDTA may be obtained from EDTA disodium dihydrate or from EDTA (viz., edetic acid). The reported acid dissociation constants for EDTA are pKa1=2.00; pKa2=2.67; pKa3=6.16; and pKa4=10.26. Handbook at 261. Accordingly, one will appreciate that EDTA sodium may be comprised of EDTA having differing ionization states depending on the pH of the formulation. Thus, the expression "EDTA sodium" refers to, for example, EDTA disodium dihydrate, as well as the EDTAs of differing ionization states.

In certain aspects, the pharmaceutical formulation may comprise disodium EDTA dihydrate in an amount of from about 0.1 mg/mL to about 1 mg/mL, including all values in between, for example, about 0.2 mg/mL, about 0.3 mg/mL, about 0.4 mg/mL, about 0.5 mg/mL, about 0.6 mg/mL, about 0.7 mg/mL, about 0.8 mg/mL, and about 0.9 mg/mL. In another embodiment, the pharmaceutical formulation comprises disodium EDTA dihydrate in an amount of about 0.2 mg/mL In certain aspects, the pharmaceutical formulation may comprise an antimicrobial effective amount of a preservative. Examples of preservatives include, but are not limited to, one or more of benzoic acid, benzyl alcohol, butylparaben, ethylparaben, methylparaben, phenoxyethanol, phenylethyl alcohol, propylene glycol, propylparaben, sorbic acid, and the like. The preservative may be a pharmaceutically acceptable salt of the preservatives contemplated herein, for example, sodium benzoate, methylparaben sodium, propylparaben sodium, potassium sorbate, and the like.

In certain aspects, the preservative comprises methylparaben or a pharmaceutically acceptable salt thereof, propyl paraben or a pharmaceutically acceptable salt thereof, or a combination thereof, for example, the preservative comprises methyl paraben and propylparaben sodium.

One may appreciate that an antimicrobial effective amount of preservative may be determined using known methods, including, for example, Chapters <51> and <61> of the USP. In certain aspects, the pharmaceutical formulation comprises from about 0.5 mg/mL to about 1.8 mg/mL of methyl paraben and all values in between, including, for example about 0.6 mg/mL, about 0.7 mg/mL, about 0.8 mg/mL, about 0.9 mg/mL, about 1.0 mg/mL, about 1.1 mg/mL, about 1.2 mg/mL, about 1.3 mg/mL, about 1.4 mg/mL, about 1.5 mg/mL, about 1.6 mg/mL, and about 1.7 mg/mL. In other aspects, the pharmaceutical formulation may comprise about 0.5 mg/mL of methylparaben and about 0.25 mg/mL of propylparaben, obtained, for example from propylparaben sodium. In yet other aspects, the pharmaceutical formulation may comprise about 0.9 mg/mL of methyl paraben and about 0.1 mg/mL propylparaben, obtained, for example from propylparaben sodium.

In other aspects, the pharmaceutical formulation may optionally comprise, a glycol, in an amount of about 1 mg/mL to about 20 mg/mL, and all values in between, including, for example about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, and about 19 mg/mL.

Examples of glycols, include, but are not limited to one or more of glycerol, propylene glycol, butylene glycol, 1,4-butanediol, pentylene glycol, 1,5-pentanediol, hexylene glycol, 1,6-hexanediol, and the like. In certain aspects, the pharmaceutical formulation may comprise propylene glycol in an amount of from about 10 mg/mL to about 20 mg/mL, and all values in between, including, for example about 11 mg/mL, about 12 mg/mL, about 13 mg/mL, about 14 mg/mL, about 15 mg/mL, about 16 mg/mL, about 17 mg/mL, and about 18 mg/mL. In another aspect, the pharmaceutical formulation may comprise propylene glycol in an amount of about 10 mg/mL In one aspect, the pharmaceutical formulation may optionally comprise a pharmaceutically acceptable buffer. Examples of pharmaceutically acceptable buffers include those capable of functioning as a buffer at the pH-values contemplated herein, which may include, for example, acetic acid, benzoic acid, ascorbic acid, citric acid, or a pharmaceutically salt thereof, for example, acetic acid and sodium acetate or citric acid and sodium citrate. Flynn identifies an exemplary listing of systemically compatible buffers and their approximate buffering ranges. Flynn at 154. The amount of buffer, if present, may be present in an amount of about 0.1 mM to about 10 mM and all values in between, including, for example about 0.2 mM, about 0.4 mM, about 0.6 mM, about 0.8 mM, about 1 mM, about 2 mM, about 4 mM, about 6 mM, and about 8 mM.

In one aspect, the pharmaceutical formulation may optionally comprise a citrate buffer in an amount of about 1 mM to about 10 mM. One may appreciate that citric acid has reported acid dissociation constants of pKa1=3.13; pKa2=4.76; and pKa3=6.40. Handbook at 181. Accordingly, one will appreciate that the expression "citrate buffer" may comprise citric acid, monobasic citrate, dibasic citrate, tribasic citrate, and a combination thereof. The fractional amount of species may depend on the pH of the formulation. Thus, the expression "citrate buffer" refers to, for example, sodium citrate, as well as the citrate species of differing ionization states.

In another aspect, the pharmaceutical formulation may optionally comprise a sufficient amount of a gelling agent. Examples of gelling agents include, but are not limited to, at least one of a carbomer, a carboxymethylcellulose or pharmaceutically acceptable salt thereof (e.g., carboxymethylcellulose sodium), a carrageenan, a chitosan, a gelatin, a guar gum, a cellulose (e.g., ethylcellulose, hydroxyethylmethylcellulose, hydroxyethylcellulose, hydroxyethylmethylcellulose, hydroxypropyl cellulose, a low-substituted hydroxypropyl cellulose, hypromellose (aka, hydroxypropyl methylcellulose ("HMPC")), methylcellulose, a poloxamer, and the like.

The amount of gelling agent, if present, may be considered a sufficient amount of gelling agent to form a gel suitable for use, for example, filling a syringe, applying said gel from a syringe, and applying said gel to a laceration. The Handbook identifies exemplary amounts of gelling agents. See, e.g., Handbook at 312, 320, 438, 507, etc. Contemplated herein are exemplary amounts of gelling agents, including for example, a carbomer (about 0.5% to about 2%), carboxymethylcellulose sodium (about 3% to about 6%), a carrageenan (about 0.3% to about 1%), a chitosan (about 0.5% to about 1%), a gelatin (about 0.5% to about 15%), a guar gum (about 0.1% to about 2%), hydroxyethylcellulose (about 1% to about 5%), hydroxyethylmethylcellulose (about 1% to about 4%), hydroxypropylcellulose (about 0.5% to about 10%), methylcellulose (about 0.5% to about 90%), a poloxamer (e.g., Poloxamer 407, about 15% to about 50%).

In certain aspects, the pharmaceutical formulation may comprise a gelling agent comprising hydroxyethylcellulose in an amount of from about 1% to about 5% and all values in between, including, for example, about 2%, about 3%, and about 4%. In one aspect, the gelling agent may comprise hydroxyethylcellulose having a grade of about 5000 cP. In other aspects, the pharmaceutical formulation may comprise a gelling agent comprising hydroxyethylcellulose in an amount of about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, and about 3.9%. In other aspects, the pharmaceutical formulation may comprise a gelling agent comprising hydroxyethylcellulose in an amount of about 17.6 mg/mL (viz., about 1.76%) or about 35.2 mg/mL (viz., about 3.52%).

In certain aspects, the pharmaceutical formulation comprises a sufficient amount (e.g., QS to volume) of water (e.g., purified water, sterile purified water, water for injection, or sterile water for injection). One may appreciate that a sufficient amount of water comprises a volume sufficient to provide the stated amounts of actives (e.g., lidocaine, epinephrine, and tetracaine).

In certain aspects, the pharmaceutical formulation has a pH of from about 3.6 to about 4.2, and all values in between, including, for example, about 3.7, about 3.8, about 3.9, about 4.0, and about 4.1. One may appreciate that a pH adjusting agent (e.g., hydrochloric acid or sodium hydroxide) may be added to adjust the pH to a desired value.

Another aspect relates to a pharmaceutical formulation comprising: a) lidocaine hydrochloride in an amount of about 40 mg/mL; b) racepinephrine hydrochloride in an amount of about 0.61 mg/mL; c) tetracaine hydrochloride in an amount of about 5 mg/mL; d) propylene glycol in an amount of about 10 mg/mL; e) sodium metabisulfite in an amount of about 0.27 mg/mL; f) a disodium salt of ethylenediaminetetraacetic acid in an amount of about 0.2 mg/mL; g) a paraben comprising methylparaben in an amount of from about 0.9 mg/mL to about 1.8 mg/mL; h) a gelling agent comprising hydroxyethylcellulose in an amount of from 0 mg/mL to about 40 mg/mL; and i) a sufficient amount of water; wherein the pharmaceutical formulation has a pH of from about 3.6 to about 4.2.

Yet another aspect relates to a pharmaceutical formulation comprising: a) lidocaine hydrochloride in an amount of about 40 mg/mL; b) racepinephrine hydrochloride in an amount of about 0.61 mg/mL; c) tetracaine hydrochloride in an amount of about 5 mg/mL; d) propylene glycol in an amount of about 10 mg/mL; e) sodium bisulfite in an amount of about 0.29 mg/mL; f) a disodium salt of ethylenediaminetetraacetic acid in an amount of about 0.2 mg/mL; g) a paraben comprising methylparaben in an amount of from about 0.9 mg/mL to about 1.8 mg/mL; h) a gelling agent comprising hydroxyethylcellulose in an amount of from 0 mg/mL to about 40 mg/mL; and i) a sufficient amount of water; wherein the pharmaceutical formulation has a pH of from about 3.6 to about 4.2.

The pharmaceutical formulations disclosed herein exhibit improved long-term stability when stored at room temperature in a syringe protected from light. For instance, results reported herein shows that pharmaceutical formulations disclosed herein exhibit an epinephrine potency of not less than ("NLT") of about 90% and not more than ("NMT") about 115% of the labeled claim when the pharmaceutical formulations are stored at room temperature (e.g., about 22° C. to about 25° C.) in a plastic syringe (e.g., a BD syringe fitted with a Luer-Lok tip, or straight tip; or a PD syringe fitted with a Luer-Lok tip or straight tip) for at least 180 days or more, including, for example, 190 days, 200 days, 210 days, 220 days, 230 days, 240 days, 250 days, 260 days, 270 days, 280 days, 290 days, 300 days, 310 days, 320 days, 330 days, 340 days, 360 days, 370 days, 380 days, 390 days, 400 days, 410 days, and 420 days. For instance, LET formulations disclosed herein maintain an epinephrine content of from about 90% to about 115% of the label claim when stored under reduced light transmission at room temperature (20-25° C.) for at least 180 days or more. Stated another way, a LET formulation having an epinephrine label claim of 0.5 mg mL (0.05%) maintains an epinephrine content of about 0.45 mg/mL (0.045%) to about 0.575 mg/mL (0.0575%) when stored under reduced light transmission at room temperature (20-25° C.) for at least 180 days or more.

Further, the LET formulations disclosed herein maintain a contents of each of lidocaine and tetracaine of from about 90% to about 110% when stored under reduced light transmission at room temperature (20-25° C.) for at least 180 days or more. And the LET formulations disclosed herein that comprise a preservative (e.g., methylparaben) have an antimicrobial effectiveness for at least 180 days or more by having a preservative (e.g., methylparaben) content of from about 80% to about 120% of the preservative label claim.

Another aspect relates to a syringe product comprising any one of the pharmaceutical formulations disclosed herein. The syringe may be fitted either with a straight tip or a Luer-Lok tip and have volumes (in mL) of: 1, 3, 5, 10, 20, 30, and 60. Typically, a 5-mL syringe (e.g., PD syringe) fitted with a straight tip may be used with a LET solution/gel volume of about 3 mL.

The syringe (e.g., PD syringe) may have an amber colorant having a reduced light transmission. Alternatively, the syringe may be enclosed in a packing material having a reduced light transmission (e.g., amber-colored film or aluminum foil). The amber colorant or packing material has a reduced light transmission of less than 5%, less than 4%, less than 3%, less than 2%, or less than 1% at any wavelength between 290 nm and 450 nm.

Yet another aspect disclosed herein relates to a method for providing procedural analgesia to a patient in need thereof, which comprises topically administering to the patient in need of analgesia any one of the pharmaceutical formulations disclosed herein. Topical administration may be applied, for example, to a patient's laceration prior to suturing.

Another aspect relates to a process for preparing any one of the pharmaceutical formulations disclosed herein, where said process comprises: a) dissolving the preservative in a vehicle comprising water for injection, a glycol, or a combination thereof to obtain a preservative solution; b) dissolving the preservative solution in water for injection to obtain a preserved water solution; c) dissolving in the preserved water solution: (i) lidocaine or a pharmaceutically acceptable salt thereof; (ii) tetracaine or a pharmaceutically acceptable salt thereof; (iii) the sulfite; (iv) the chelating agent; and optionally, (v) the pharmaceutically acceptable buffer; d) optionally, adjusting the pH of the step c) solution to a pH of from about 3.6 to about 4.2; e) dissolving epinephrine or a pharmaceutically acceptable salt thereof in the step c) solution or the step d) solution; f) optionally, adjusting the pH of the step e) solution to a pH of from about 3.6 to about 4.2; and g) optionally adding the gelling agent to the step e) solution or the step f) solution. Said process may further comprise protecting the actives (e.g., epinephrine) from light during the manufacture process. Said light protection may be achieved using a suitable covering or may be achieved by working in the dark.

It is understood that the process for preparing the ready to use LET formulation disclosed herein does not utilize deoxygenated water. Further, no precautions are taken to exclude molecular oxygen from the containers and syringes that contain the ready to use LET formulation. Thus, one will appreciate that the LET formulations disclosed herein may further comprise a dissolved amount of molecular oxygen present in the water. With the understanding that oxygen solubility in water is about 40 mg/L (≈25° C. and ≈1 bar), the ready to use liquid formulations disclosed herein may further comprise about 40 mg/L of oxygen.

Aspects of the ready to use LET formulations are exemplified below. The exemplified embodiments should not be used to limit the scope of the claimed subject matter.

EXAMPLES

The text that follows may include abbreviated terms. For ease of reference, the following table correlates numerous abbreviated terms utilized herein along with the unabridged names.

| Abbreviated Terms | Names |
|---|---|
| AET | Antimicrobial Effectiveness Tests |
| EDTA | Ethylenediaminetetraacetic acid |
| Na₂EDTA DH | Disodium salt of ethylenediaminetetraacetic acid dihydrate |
| Epi BT | Epinephrine Bitartrate |
| Epi HCl | Epinephrine Hydrochloride |
| Epi FB | Epinephrine Free Base |
| EVA | Ethylene-vinyl acetate |
| HEC | Hydroxyethylcellulose |
| LET | Lidocaine, Epinephrine, Tetracaine |
| Lido HCl | Lidocaine Hydrochloride |
| Lido HCl MH | Lidocaine Hydrochloride Monohydrate |
| MP | Methylparaben |
| NAC | N-acetylcysteine |
| NaPP | Propylparaben sodium |
| ND | Not determined |
| PES | Polyethersulfone |
| PG | Propylene glycol |
| PP | Propylparaben |
| PVC | Polyvinyl chloride |
| PW | Preserved Water |
| RT | Room Temperature |
| SBS MH | Sodium bisulfite monohydrate |
| SBS | Sodium bisulfite |
| SMBS | Sodium metabisulfite |
| Soln | Solution |
| SWFI | Sterile Water for Injection |
| Tet HCl | Tetracaine Hydrochloride |

Syringes described herein are available commercially from, for example, Becton, Dickinson and Company (e.g., BD syringes) or Medisca (e.g., PD syringes). Syringes contemplated herein include, for example, PreciseDose Dispenser™ Syringe, Amber, 5 mL with Tip Cap for Oral/Topical use (e.g., PD syringes). The syringes may be fitted with a either a straight tip or a Luer-Lok tip and have volumes (in mL) of: 1, 3, 5, 10, 20, 30, and 60. Typically, 5-mL amber syringes fitted with a straight tip are used with a LET solution/gel volume of about 3 mL.

Potencies for each of lidocaine, epinephrine, tetracaine, and paraben (e.g., methylparaben and propylparaben) may be determined using published procedures. See, e.g., USP 43 and Sabatier. Potencies reported herein were determined using a Waters Acquity H Class UPLC with TUV or PDA Detector equipped with a Luna C18(2), 5 μm, 150×4.6 mm column operating at column temperature of about 45° C. with a flow rate of about 1 mL/min and an injection volume of about 4 μL (UV detection of about 220 nm).

Chromatograms were run using a gradient method comprising Mobile Phase A and Mobile Phase B (acetonitrile), as shown below.

| Time, min | Mobile phase A, % | Mobile phase B, % |
|---|---|---|
| 0.0 | 80.0 | 20.0 |
| 14.0 | 55.0 | 45.0 |
| 15.0 | 80.0 | 20.0 |
| 20.0 | 80.0 | 20.0 |

Mobile Phase A comprised a solution comprising about 3.0 g of 1-heptanesulphonic acid sodium salt in 1000 mL of purified water having a pH of about pH 3.0±0.1 (adjusted with phosphoric acid solution). Selected components of the system (e.g., seal wash, purge, and needle wash) were flushed using a 50:50 methanol water solution.

Working standards and samples were prepared as follows with the understanding that alternative weights and/or volumes may be employed in the preparation of solutions; provided that the changes are made in the same proportion and that the final concentrations/ratios are the same. See USP General Notices. Where possible, use low actinic glassware and protect solutions from light. Alternatively, clear flasks may be used for sample preparations where light protection may be achieved using either aluminum foil or working in the dark.

Standard stock solutions for working and/or check standards are described in the text that follows.

Preparation of Epinephrine Bitartrate Stock Solution
1. Accurately weigh about 45 mg of Epinephrine Bitartrate USP standard.
2. Transfer the Epinephrine Bitartrate USP standard into 100.0 mL volumetric flask using about 50 mL Diluent.
3. Sonicate for 5 min and cool to room temperature.
4. Dilute to volume with diluent. Mix well to form Epinephrine Bitartrate Stock Standard Solution.

As a point of reference, the Diluent used herein comprises a solution of 500 mL methanol and 0.001 N HCl. The concentration of Epinephrine Bitartrate Stock Standard Solution is about 250 mcg/mL of epinephrine free base.

Preparation of Tetracaine HCl Stock Standard Solution
1. Accurately weigh about 25 mg of Tetracaine HCl USP standard.
2. Transfer the Tetracaine HCl USP standard into 100.0 mL volumetric flask using about 50 mL Diluent.
3. Sonicate for 5 min and cool to room temperature.
4. Dilute to volume with Diluent. Mix well to form Tetracaine HCl Stock Standard Solution.

The concentration of Tetracaine HCl Stock Standard Solution is about 250 mcg/mL of Tetracaine HCl.

Preparation of Methylparaben Stock Standard Solution
1. Accurately weigh about 45 mg of Methylparaben USP standard.
2. Transfer Methylparaben USP standard into 50.0 mL volumetric flask using about 20 mL Diluent.
3. Sonicate for 5 min and cool to room temperature.
4. Dilute to volume with Diluent. Mix well to form Methylparaben Stock Standard Solution.

The concentration of Methylparaben Stock Standard Solution is about 900 mcg/mL of methylparaben.

Preparation of LET Working Standard Solution
1. Accurately weigh about 20 mg of Lidocaine HCl USP.
2. Transfer the Lidocaine HCl USP standard into 50.0 mL volumetric flask using about 20 mL Diluent.
3. Sonicate for 5 min and cool to room temperature.
4. Transfer 1.00 mL of Epinephrine Bitartrate Stock Standard Solution, 1.00 mL of Methylparaben Stock Solution and 10.0 mL of Tetracaine HCl Stock Standard Solution into same 50.0 mL volumetric flask.
5. Dilute to volume with Diluent and mix well to form the Working Standard Solution. The concentration of epinephrine free base is about 5 mcg/mL, the concentration of Tetracaine HCl is about 50 mcg/mL, the concentration of Methyl Paraben is about 18 mcg/mL and the concentration of Lidocaine HCl is about 0.4 mg/mL in the Working Standard Solution.

Preparation of LET Sample
1. Place 100.0 mL Volumetric Flask into a balance and tare it to zero.
2. Transfer about 1 mL of the LET sample into the flask making sure that all sample is on the bottom of the flask, not on the flask walls.
3. Add about 50 mL of Methanol.
4. If necessary, vortex the solution for about 2 minutes (to disintegrate gelling agent).

5. Depending on the gelling agent content, sonicate for about 10 minutes to about 30 minutes until the LET sample is completely in solution.
6. Add about 20 mL of 0.001 N HCl.
7. Vortex the solution for about 2 minutes.
8. If necessary, sonicate for at least about 30 minutes.
9. Equilibrate the clear solution to room temperature.
10. Dilute to volume with 0.001 N HCl. Mix well.

The concentration of Epinephrine base is about 5 mcg/mL, the concentration of Tetracaine HCl is about 50 mcg/mL, concentration of methylparaben is about 18 mcg/mL, and the concentration of Lidocaine HCl is about 0.4 mg/mL in the LET sample. N.B. A clear flask may be used for the LET sample preparations with protection of aluminum foil.

Chromatographic Analysis

Equilibrate the chromatographic system. The baseline should have minimal noise and drift. The injection sequence includes the following properties:
a. Make one injection of Diluent and five injections of the Working standard at the beginning of the analysis.
b. Make one injection of Check standard.
c. Make sample preparation injection(s). NMT ten samples may be injected before the bracketing standard. Working Standard will be use as Bracketing Standard.
d. Make one injection of working standard as End standard at the end of sequence.

The chromatographic system found to be suitable, when one or more of the following parameters are satisfied: (i) % RSD of peak area from the first five injections of the working standard solution of not more than ("NMT") 2.0%, (ii) an absolute difference between the mean working and check standard peak area is NMT 2.0%), and (iii) the % Recovery of all bracketing injections against mean of working standard solution peak area throughout the run range from about 98 to about 102%.

Calculated Potencies

Calculate the potency for each of Epinephrine (Eqn. 1), Lidocaine HCl (Eqn. 2), Tetracaine HCl (Eqn. 3), and methylparaben (Eqn. 4) as follows:

$$\frac{\text{Area of Sample Preparation}}{\text{Average Area of Standard preparation}} \times C \times \frac{P}{100\%} \times \frac{100.0 \text{ mL} \times SG}{\text{sample mass, g}} \times \frac{1}{0.5 \text{ mg}} \times 0.54967 \times 100\% \quad (1)$$

$$\frac{\text{Area of Sample Preparation}}{\text{Average Area of Standard preparations}} \times C \times \frac{100.0 \text{ mL} \times SG}{\text{sample mass, g}} \times \frac{P}{100\%} \times \frac{1}{40 \text{ mg}} \times 100\% \quad (2)$$

$$\frac{\text{Area of Sample Preparation}}{\text{Average Area of Standard preparations}} \times C \times \frac{100.0 \text{ mL} \times SG}{\text{sample mass, g}} \times \frac{P}{100\%} \times \frac{1}{5 \text{ mg}} \times 100\% \quad (3)$$

$$\frac{\text{Area of Sample Preparation}}{\text{Average Area of Standard preparations}} \times C \times \frac{100.0 \text{ mL} \times SG}{\text{sample mass, g}} \times \frac{P}{100\%} \times \frac{1}{1.8 \text{ mg}} \times 100\% \quad (4)$$

For the Epinephrine Potency (viz., Eqn. 1), C is the Standard concentration, mg/mL; P is the Standard potency, %; 0.54967=183.20/333.29 where 183.20 and 333.29 are the molecular weights of Epinephrine base and Epinephrine Bitartrate; 0.5 mg is the epinephrine labeled content; and SG is the LET sample specific gravity, which may be, for example, 1.0 for a LET solution, 1.03 for LET gel (e.g., 17.6 mg/mL of HEC), and 1.05 for LET gel (e.g., 35.2 mg/mL HEC).

For the Lidocaine HCl Potency (viz., Eqn. 2), C is the Standard concentration, mg/mL; P is the Standard potency, %; 40 mg is Lidocaine HCl labeled content; and SG is the LET sample specific gravity, which may be, for example, 1.0 for a LET solution, 1.03 for LET gel (e.g., 17.6 mg/mL of HEC), and 1.05 for LET gel (e.g., 35.2 mg/mL HEC).

For the Tetracaine HCl Potency (viz., Eqn. 3), C is the Standard concentration, mg/mL; P is the Standard potency, %; 5 mg is Tetracaine HCl labeled content; and SG is the LET sample specific gravity, which may be, for example, 1.0 for a LET solution, 1.03 for LET gel (e.g., 17.6 mg/mL of HEC), and 1.05 for LET gel (e.g., 35.2 mg/mL HEC).

For the Methylparaben Potency (viz., Eqn. 4), C is the Standard concentration, mg/mL; P is the Standard potency, %; 1.8 mg is methylparaben labeled content; and SG is the LET sample specific gravity, which may be, for example, 1.0 for a LET solution, 1.03 for LET gel (e.g., 17.6 mg/mL of HEC), and 1.05 for LET gel (e.g., 35.2 mg/mL HEC).

The examples that follow serve to illustrate aspects of the LET formulations disclosed herein and are not mean to be limiting with respect to the LET formulations claimed herein. As stated herein, LET formulations may be protected from light by storage in a suitable light protected container.

Example 1. Preparation LET Formulations (Gels) 1-3

A starting point for the development work involved generally modifying the USP 43 LET topical product (pH 3.2-4.2) by (1) reducing the pH to about 2, (2) adding propylene glycol, and (3) modifying the amount of sulfite (e.g., sodium bisulfite).

Preserved water ("PW") 1 was prepared by mixing 2 mL water for injection (WFI) with 2 mL propylene glycol ("PG") in a 20 mL glass vial. Methylparaben ("MP," 50.5 mg) and propylparaben ("PP," 25 mg) were added to the glass vial containing WFI and PG with about 45 minutes of constant stirring to achieve a clear paraben solution. In a 125 mL glass flask, 80 mL of WFI were added along with the paraben solution. A sufficient amount (Qs) of WFI was added to obtain 100 mL, which had a pH of 5.776. The pH was adjusted to 4.421 using 10% HCl. PW No. 1 was filtered using a 5 micron filter.

PW No. 2 was prepared by adding 80 mL of WFI to a 125 mL glass flask. Propylparaben sodium ("NaPP," 28.5 mg) was added to the flask, which dissolved immediately. The pH of the NaPP solution was 9.555. The pH was adjusted to 4.425 using 10% HCl. It should be noted that PP has a pKa of about 8.4 at 22° C. Handbook at 596. Thus, pH adjustment to about 4.4 results in the formation of PP. MP (50.6 mg) was added to said glass flask and stirred for about 35 minutes. The solution was cloudy with no visible particles. A sufficient amount of WFI was added to achieve a volume of 100 mL. Although the solution was stirred for an additional 30 minutes, fine powders were observed.

PW No. 3 was prepared by adding 80 mL of WFI to a 125 mL glass flask. NaPP (28.5 mg) was added to the flask, which dissolved immediate. The pH of the NaPP solution was 9.556. The pH was adjusted to 4.094 using 10% HCl. To a glass vial (20 mL), 2 mL each of WFI and PG were added and mixed well. MP (50.6 mg) was added to said glass vial and stirred for about 30 minutes to achieve complete dissolution. The MP solution was transferred to the PP solution.

A sufficient amount of WFI was added to achieve a volume of 100 mL. The final pH was 4.283.

Table 1 summarizes the compositional makeup of PW Nos. 1-3, as well as the potencies for methylparaben (MP) and propylparaben (PP) after manufacture.

TABLE 1

Compositional makeup of Preserved Water 1-3

| | Preserved Water 1-3 | | |
|---|---|---|---|
| | 1 | 2 | 3 |
| Ingredients | Amount (mg/mL) | | |
| Propylene glycol | 20 | — | 20 |
| Methylparaben | 0.5 | 0.5 | 0.5 |
| Propylparaben | 0.25 | — | — |
| Propylparaben Sodium[a] | — | 0.25 | 0.25 |
| Water for Injection | QS | QS | QS |
| pH Adjuster (10% HCl) | QS | QS | QS |
| pH | 4.421 | 4.425 | 4.283 |
| MP Potency (%) | 95.2 | 100.8 | 102.1 |
| PP Potency (%) | 95.1 | 90.9 | 92.9 |

Note:
[a] Reported amounts are based on PP.

PW Nos. 1-3 were used to manufacture LET Formulations 1-3, respectively. The typical manufacturing procedure is as follows. Wrap a 100 mL beaker with an amber bag and add 45 mL (75% of total amount) of preserved water to the beaker. Add lidocaine HCl monohydrate ("Lido HCl MH," 2.400 g±0.048 g), racepinephrine HCl ("Epi HCl," 30 mg±0.6 mg), tetracaine HCl ("Tet HCl," 300 mg±6 mg), and sodium bisulfite monohydrate ("SBS MH," 180.0 mg±3.6 mg) to the beaker with stirring. Added about 9 mL of preserved water (about 90% of total amount) and stirred for at least about 30 minutes to complete dissolution. Observed and reported pH and sift hydroxyethylcellulose ("HEC," 1.056 g±0.021 g) with vigorous agitation and rinse the container with about 3 mL of preserved water. The HEC grade used herein was 5000 cP NF. Continue stirring the solution for at least about 6 hours, QS to 60 mL (final volume) with preserved water and stir for 30 minutes. Observe and record pH values. Add 3 mL of LET gels to 5 mL amber syringe. Initial epinephrine potencies were determined for each LET gel. Table 2 summarizes the compositional makeup for LET Formulations (Gels) 1-3.

TABLE 2

Compositional makeup of LET Formulations (Gels) 1-3

| | LET Formulations 1-3 | | |
|---|---|---|---|
| | 1 | 2 | 3 |
| Ingredients | Amount (mg/mL) | | |
| Lido HCl | 40 | 40 | 40 |
| Epi HCl | 0.5 | 0.5 | 0.5 |
| Tet HCl | 5 | 5 | 5 |
| PG | 20 | — | 20 |
| SBS MH | 3 | 3 | 3 |
| MP | 0.5 | 0.5 | 0.5 |
| PP | 0.25 | — | — |
| NaPp[a] | — | 0.25 | 0.25 |
| HEC | 17.6 | 17.6 | 17.6 |
| PW No. 1 | QS to 60 mL | — | — |
| PW No. 2 | — | QS to 60 mL | — |
| PW No. 3 | — | — | QS to 60 mL |
| pH | 2.110 | 2.107 | 2.101 |
| Epi. Pot. | 102.3 | 102.2 | 100.8 |

Note:
[a] Reported amounts are based on PP.

The LET gels provided a beyond-use date ("BUD") of 90 days when stored in 5 mL amber syringes at room temperature (protected from light). Although the reduced pH improved the stability relative to the USP 43 LET topical product, the pH of about 2 was considered too low because application of the gel to the skin resulted in an increased burning sensation due to the decreased pH.

It should be noted that the ratio of mass amount (in mg) of epinephrine free base to the mole amount of sulfur in the sulfite (viz., sodium bisulfite monohydrate) is 172. For the USP 43 topical gel, the ratio of mass amount (in mg) of epinephrine free base to the mole amount of sulfur in the sulfite (viz., sodium bisulfite) is 29.

Example 2. Investigation of Propylparaben Adsorption

During the foregoing development activities, it was noted that the propylparaben content may be lower than expected. Accordingly, an investigation was conducted to determine the source of propylparaben content variability.

PW 4 was prepared by mixing 40 mL sterile water for injection (SWFI) with 40 mL PG in a 250 mL glass beaker. MP (1000 mg±20 mg) and PP (500 mg±10 mg) were added to the glass beaker containing SWFI and PG with about 45 minutes of constant stirring at 500 rpm to achieve paraben solution. It should be noted that the solution was cloudy. In a 4 L glass beaker, add 1800 mL SWFI and paraben solution with stirring for about 30 minutes. The pH was adjusted to about 4.2 (4.0 to 4.5) using 10% HCl. A sufficient amount (QS) of SWFI was added to obtain 2000 mL, which was mixed for about 5 minutes. The observed and recorded pH was 4.279. PW No. 4 was filtered using a 0.2 micron polyethersulfone ("PES") filter and transferred into a 2 L ethylene-vinyl acetate (EVA) bag. Based on this information, it was determined that it may be helpful to dissolve PP first prior to the addition of MP.

PW No. 5 was prepared by adding 1800 mL of SWFI to a 4 L glass beaker. NaPP (560 mg±11 mg) was added to the flask, which dissolved immediately. The pH of the NaPP solution was adjusted to 4.232 using 10% HCl. MP (1000 mg±20 mg) was added to said beaker and stirred for about 45 minutes. The solution was cloudy with no visible particles. A sufficient amount of WFI was added to achieve a volume of 2000 mL, which was mixed for about 30 minutes. Fine particles remained in the solution. The observed and recorded pH was 4.276. PW No. 5 was filtered using a 0.2 micron PES filter and transferred into a 2 L ethylene-vinyl acetate (EVA) bag.

PW No. 6 was prepared by adding 40 mL of SWFI and 40 mL PG to a 100 mL beaker; the liquid was mixed well. MP (1000 mg±20 mg) was added to the beaker and the liquid was stirred by mixer for at least 45 minutes to obtain a clear solution. To a 4 L beaker was added 1700 mL SWFI and NaPP (560 mg±11 mg) and mixed for about 2 minutes. The pH of the NaPP sodium solution was adjusted to 4.202 using 10% HCl (about 2.5 mL). The MP solution was transferred to the PP solution in the 4 L beaker. The solution volume was adjusted to 2000 mL and mixed for 5 minutes. The observed and recorded pH was 4.280. PW No. 6 was filtered using a 0.2 micron PES filter and transferred into a 2 L EVA bag.

Table 3 summarizes the compositional makeup of PW Nos. 4-5, as well as the PP potencies after day one (1D) and day two (2D).

TABLE 3

Compositional makeup of Preserved Water 4-5

| | Preserved Water 4-6 | | |
|---|---|---|---|
| Ingredients | 4 | 5 | 6 |
| | Amount (mg/mL) | | |
| Propylene glycol | 20 | — | 20 |
| Methylparaben | 0.5 | 0.5 | 0.5 |
| Propylparaben | 0.25 | — | — |
| Propylparaben Sodium[a] | — | 0.25 | 0.25 |
| Sterile Water for Injection | QS | QS | QS |
| pH Adjuster (10% HCl) | QS | QS | QS |
| pH | 4.279 | 4.276 | 4.280 |
| PP Potency (%), 1D | 68.7 | 64.90 | 68.96 |
| PP Potency (%), 2D | 58.41 | 54.60 | 58.96 |

Note:
[a]Reported amounts are based on PP.

The data shows that the observed potencies for propylparaben decrease substantially after 1-2 days.

Additional preserved water (viz., PW No. 4-2) was manufactured similarly to PW 4 to investigate the source of the loss of propylparaben potency. Samples of PW4-2 were prepared and analyzed under different conditions.

TABLE 4

Investigation of Reduced Propylparaben Potencies

| No. | Condition | Initial | Potency Values† |
|---|---|---|---|
| A | Unfiltered in Syringe | PP: 97.97% | MP: 98.2%, PP:91.3% |
| B | Filtered in EVA bag (2 L) within one hr. | PP: 91.62% | MP: 85.9%, PP: 40.4% |
| C | Filtered in beaker then transfer into Syringe | PP: 97.53% | MP: 96.9%, PP: 86.1% |
| D | Filtered in IV bag | PP: 96.49% | MP: 95.6%, PP: 83.8% |
| E | Filtered in PVC free 100 ml bag (EVA bag) | PP: 93.6% | MP: 95.1%, PP: 86.9% |

†Day 6: Potencies for bag samples (4 D in bag and 2 D in Syr). Potencies for syringe samples are 6 D.

Based on the above-mentioned investigation, it was concluded that PP-EVA surface adsorption occurred, thereby resulting in reduced PP potency values. In view of the foregoing, therefore, care should be taken to use an alternative material (such as, glass (rather than EVA)) when PP is used for the manufacture of a LET formulation. A suitable light protected PreciseDose Dispenser™ Syringe with Tip Cap may be used as a product container when using PP. Additionally, a glass container may be used for preparation and storage of PW. In the absence of added PG, NaPP dissolved immediately but MP may be slow to dissolve and may require a dissolution time of up to 16 hours at RT. In the presence of PG, MP and PP dissolution times reduced substantially (e.g., from about 5 to about 6 hours, including heating/cooling) to about 1 hour at RT.

Example 3. Preparation of LET Formulations (Gels) 4-5

In view of the foregoing, preserved water containing PP was maintained in a glass beaker in support of the manufacture of LET gels 4-5.

Preserved Water ("PW") No. 7 used in the manufacture of LET gels 4-5 was prepared by adding 8 mL of SWFI and 8 mL PG to a 250 mL beaker; the liquid was mixed well. MP (200 mg+4 mg) was added to the beaker and the liquid was stirred by mixer for at least 30 minutes to obtain a clear solution. To a 500 mL beaker was added 320 mL SWFI and NaPP (112 mg±2 mg) and mixed for about 2 minutes. The pH of the NaPP solution was adjusted to 4.228 using 10% HCl (about 0.1 mL). The MP solution was transferred to the PP solution in the 500 mL beaker the beaker holding the MP solution was rinsed with 20 mL SWFI. The resultant solution was mixed for about 10 minutes and the pH further adjusted using 10% HCl to provide a pH of 4.135. Add a sufficient amount of SWFI to obtain a final volume of 400 mL, which was mixed for several minutes. The solution was maintained in the 500 mL beaker.

LET gel 4 was manufactured as follows. Wrap a 300 mL beaker with an amber bag and add 75 mL (75% of total) with PW No. 7. Add Lido HCl MH (4.00 g±0.08 g) to the beaker, dissolve, and then add Tet HCl (500 mg±10 mg) and stir (315 rpm) for at least about 15 minutes. The pH of the solution was 4.508. Adjust the pH to 4.269 using 0.1 N HCl. Add sodium metabisulfite ("SMB," 21.6 mg±0.4 mg), dissolve, add Epi HCl (50 mg±1 mg) with stirring. Recorded pH of 4.269. Added 10 mL of PW No. 7 and stirred for at least about 15 minutes. Observe and record the pH (4.272). Sift the HEC (1.76 g±0.04 g) into the solution under vigorous agitation and rinse the container with 10 mL PW No. 7. Continue stirring for at least about 60 minutes. Add PW No. 7 to achieve a final volume of 100 mL and stir for at least about 5 minutes. Fill 6×5 mL amber syringe with 3 mL LET gel 4 and 2×20 mL glass vials (protected from light).

LET gel 5 was manufactured as follows. Wrap a 300 mL beaker with an amber bag and add 75 mL (75% of total) with PW No. 7. Add Lido HCl MH (4.00 g±0.08 g) to the beaker, dissolve, and then add Tet HCl (500 mg±10 mg) and stir (315 rpm) for at least about 15 minutes. Adjust the pH to 4.259 using 0.1 N HCl. Add sodium metabisulfite ("SMBS," 21.6 mg±0.4 mg), dissolve, add Epi HCl (50 mg±1 mg), and N-acetylcysteine ("NAC," 51.6 mg±1 mg) with stirring. QS to 90 mL (90% of total) with PW No. 7 and stirred for at least about 15 minutes. Observed pH of 3.274 and adjusted pH to 4.207 using 10% NaOH. Sifted the HEC (1.76 g±0.04 g) into the solution under vigorous agitation and rinse the container with 10 mL PW No. 7. Continued stirring for at least about 60 minutes. Added PW No. 7 to achieve a final volume of 100 mL and stir for at least about 15 minutes. Fill 6×5 mL amber syringe with 3 mL LET gel 5 and 2×20 mL glass vials (protected from light).

TABLE 5

Compositional makeup of LET Formulations (Gels) 4-5

| | LET Formulations 4-5 | |
|---|---|---|
| Ingredients | 4 | 5 |
| | Amount (mg/mL | |
| Lido HCl | 37.5 | 37.5 |
| Epi HCl | 0.5 | 0.5 |

TABLE 5-continued

Compositional makeup of LET Formulations (Gels) 4-5

| | LET Formulations 4-5 | |
|---|---|---|
| | 4 | 5 |
| Ingredients | Amount (mg/mL) | |
| Tet HCl | 5 | 5 |
| PG | 20 | 20 |
| SMBS | 0.216 | 0.216 |
| NAC | — | 0.516 |
| MP | 0.5 | 0.5 |
| NaPp[a] | 0.25 | 0.25 |
| HEC | 17.6 | 17.6 |
| pH Adj. | QS to pH 4.272 | QS to pH 4.207 |
| PW No. 7 | QS to 100 mL | QS to 100 mL |
| Epi. Pot. | 97.1 | 100.0 |

Note:
[a]Reported amounts are based on PP.

In view of the foregoing, it was determined that initial epinephrine potency was suitable at a pH of about 4.2.

LET gels 4-5 were tested for potency, sterility (per USP<71>), and endotoxins (per USP<85>). Let gels 4-5 met or exceeded initial potency, sterility, and endotoxin levels. It should be noted that the ratio of mass amount (in mg) of epinephrine free base to the mole amount of sulfur in the sulfite (viz., sodium bisulfite monohydrate) is 183.

Example 4. Preparation of LET Formulations (Gels) 6-8

As a part of the ongoing development work, LET gels containing varying amounts of gelling agent (e.g., HEC) were prepared, as described below.

Add PG (5.00 g±0.01 g), MP (250 mg±5 mg), and PP (125.0 mg±2.5 mg) to a 20 mL glass vial with stirring for about 30 minutes.

In a 500 mL glass flask, add 350 mL SWFI, and pour the paraben solution into the flask. Rinse the residual paraben solution remaining in the 20 mL glass vial with portions of SWFI (totaling 100 mL) and transfer rinses to the 500 mL glass flask.

Add Lido HCl MH (21.33 g±0.43 g), SBS (1.50 g±0.03 g), Tet HCl (2.50 g±0.05 g), and Epi HCl (300 mg±6 mg) powders to the glass flask. Stirred using stir bar for at least about 30 minutes. Adjusted pH to 4.132 using 10% HCl and/or 10% NaOH. Added a sufficient amount of SWFI to produce final volume of 500 mL and filter solution using 0.2 micron PES filter to obtain filtered LET solution, which was used for the preparation of LET gels containing varying amounts of gelling agent (e.g., HEC).

To make the gels, added 90 mL of LET solution to three separate 300 mL beakers. For LET Formulation (Gel) 6, a homogeneous gel was obtained by slowly adding HEC 5000 cP (1.76 g±0.04 g) to the beaker under stirring using mixer (300-350 rpm) for at least about 60 minutes. For LET Formulations (Gels) 7-8, an identical process was used except that the amounts of HEC differed, e.g., HEC (3.50 g±0.07 g, LET Formulation 7, thick gel) and HEC (4.50 g±0.09 g, LET Formulation 8, thicker gel). Amber colored syringes (5 mL) were filled with 3 mL of LET gels and evaluated for potency, stability, sterility, and endotoxins. Table 6 summarizes the compositional makeup of t LET Formulations (Gels) 6-8.

TABLE 6

Compositional makeup of LET Formulations (Gels) 6-8

| | LET Formulations 6-8 | | |
|---|---|---|---|
| | 6 | 7 | 8 |
| Ingredient | Amount (mg/mL) | | |
| Lido HCl | 40 | 40 | 40 |
| Epi HCl[a] | 0.6 | 0.6 | 0.6 |
| Tet HCl | 5 | 5 | 5 |
| PG | 10 | 10 | 10 |
| SBS | 3 | 3 | 3 |
| MP | 0.5 | 0.5 | 0.5 |
| PP | 0.25 | 0.25 | 0.25 |
| HEC | 17.6 | 35 | 45 |
| SWFI | QS to 100 mL | QS to 100 mL | QS to 100 mL |
| pH Adj. | QS to pH 4.132 | QS to pH 4.132 | QS to pH 4.132 |
| Epi. Pot.[b] | 97.6 (91.8) | ND | ND |
| MP Pot.[b] | 97.2 (87.3) | ND | ND |
| PP Pot.[b] | 90.3 (82.5) | ND | ND |

Notes:
[a]Amount of epinephrine free base of about 0.5 mg/mL.
[b]Potency testing date initially and 45 D (in parenthetical).

LET Formulations (Gels) 6-8 were tested for potency, sterility (per USP<71>), and endotoxins (per USP<85>). LET Formulations (Gels) 6-8 met or exceeded initial potency, sterility, and endotoxin levels. Epinephrine potency testing (room temperature) for LET Formulation 6 samples showed an epinephrine potency of about 92% with the appearance of a light brown color, suggesting the formation of an undesirable amount of adrenochrome. It should be noted that the ratio of mass amount (in mg) of epinephrine free base to the mole amount of sulfur in the sulfite (viz., sodium bisulfite monohydrate) is about 17. The higher amount of gelling agent for the LET Formulation (Gel) 8 resulted in an increase viscosity, which complicates syringe filling.

Example 5. Preparation of LET Formulations (Gels) 9-11

As a part of the ongoing development work, LET gels were prepared containing either (i) MP with no added PP or PG (Ex. Nos. 9-10) or (ii) MP and PP with added PG, as described below.

LET Formulations (Gels) 9-10 were prepared as follows.

In a 500 mL glass flask, add 350 mL SWFI and MP (900 mg±18 mg) to the flask with stirring for at least about 1 hour; not all MP dissolved. The solution was heated from about 40° C. to about 50° C. with stirring for about 1 hour; the MP dissolved with heating. Allowing the solution to cool overnight resulted in the formation of a fine precipitate. An additional amount of SWFI was added and heated for about 40° C. to about 50° C. with stirring to obtain the MP solution.

Add Lido HCl MH (21.33 g±0.43 g), SBS (1.50 g±0.03 g), Tet HCl (2.50 g±0.05 g), and Epi HCl (302 mg±6 mg) to the flask with stirring for at least about 30 minutes. The pH was adjusted to 4.086 using 10% NaOH. QS to 500 mL using SWFI and stirred LET solutions for 5 minutes followed by filtering the solution using a 0.2 micron PES filter.

The appropriate amount of HEC (1.76 g±0.04 g for Ex. 9 and 3.50 g±0.07 g for Ex. 10) was slowly adding with sifting to two separate containers containing 90 mL of the LET solution under stirring using mixer (300-350 rpm) for at least about 60 minutes. The LET gels were finalized by adding LET solution (QS to 100 mL) with mixing for about 5 minutes. Amber colored syringes (5 mL) were filled with 3 mL of LET gels.

As a part of the preparation of the LET Formulations (Gels) 9-10, it was determined that epinephrine addition should occur after pH adjustment of lidocaine/sulfite/tetracaine solution.

LET Formulation (Gel) 11 was prepared as follows.

Add PG (5.00 g±0.01 g), MP (450 mg±9 mg), and PP (50 mg±1 mg) to a 20 mL glass vial with stirring for about 30 minutes.

In a 500 mL glass flask, add 350 mL SWFI, and pour the paraben solution into the flask. Rinse the residual paraben solution remaining in the 20 mL glass vial with portions of SWFI (totaling 100 mL) and transfer rinses to the 500 mL glass flask. Adjust pH to 4.0-4.2 using 0.1 N HCl. And obtain PW by filtering with 0.2 micron PES filter.

In a glass beaker containing 90 mL PW, add Lido HCl MH (4.266 g±0.085 g), SBS (300 mg±6 mg), and Tet HCl (500 mg±10 mg) powders to the glass flask. Stir using stir bar for at least about 15 minutes. Adjusted pH to 4.1 (4.0-4.2) using 10% NaOH (about 1.6 mL), and then add Epi HCl (61.0 mg±1.2 mg) under stirring; observed and recorded pH to be 4.043.

LET gel obtained by slowly adding sifted HEC 5000 cP (1.76 g±0.04 g) to the beaker under stirring using mixer (300-350 rpm) for at least about 60 minutes. QS with PW to 100 mL and mix for about 5 minutes. Amber colored syringes (5 mL) were filled with 3 mL of LET gels. Table 7 summarizes the compositional makeup of the LET Formulations (Gels) 9-11.

TABLE 7

Compositional makeup of LET Formulations (Gels) 9-11

| Ingredients | LET Formulations 9-11 | | |
|---|---|---|---|
| | 9 | 10 | 11 |
| | Amount (mg/mL) | | |
| Lido HCl | 40 | 40 | 40 |
| Epi HCl[a] | 0.60 | 0.60 | 0.61 |
| Tet HCl | 5 | 5 | 5 |
| PG | — | — | 10 |
| SBS | 3 | 3 | 3 |
| MP | 1.8 | 1.8 | 0.9 |
| PP | — | — | 0.1 |
| HEC | 17.6 | 17.6 | 17.6 |
| SWFI | QS | QS | QS |
| pH Adj. | QS to pH 4.086 | | Qs to pH 4.043 |
| Epi. Pot.[b] | 97.7 (91.9) | ND | 93.9 (93.9) |
| MP Pot.[b] | 96.5 (97.1) | ND | 98.4 (91.0) |
| PP Pot.[b] | N/A | ND | (98.0) 76.6 |

Notes:
[a] Amount of epinephrine free base of about 0.5 mg/mL.
[b] Potency testing date initially and 45 D (in parenthetical).

LET Formulations (Gels) 9-11 were tested for potency, sterility (per USP<71>), and endotoxins (per USP<85>). LET Formulations (Gels) 9-11 met or exceeded initial potency, sterility, and endotoxin levels. Epinephrine potency testing (room temperature at 45 days) for LET Formulations 9 and 11 showed an epinephrine potency of about 92% to about 94% with the appearance of a light brown color, suggesting the formation of an undesirable amount of adrenochrome. It should be noted that the ratio of mass amount (in mg) of epinephrine free base to the mole amount of sulfur in the sulfite (viz., sodium bisulfite monohydrate) is 17.4-17.7. The addition of PG improved preparation of PW; especially, considering dissolution of MP and/or PP in SWFI alone.

Example 6. Preparation of LET Formulations (Gels) 12-14

Separate development work (Leeah) showed that epinephrine stability may be improved by controlling the amount of sulfite (e.g., sodium metabisulfite) relative to epinephrine, as well as the amount of EDTA relative to epinephrine. Accordingly, it was of interest to investigate whether improved epinephrine stability may be achieved in the LET gels under development by controlling the amount of sulfite and EDTA, while decreasing the pH to about 3.8. It was also of interest to evaluate reducing the amount of propylparaben preservative. As the amounts of propylparaben preservative vary, the preparative methods for the preserved waters different slightly. The information that follows describes the manufacturing details for LET Formulations (Gels) 12-14.

Preparation of LET Formulation (Gel) 12.

PG (5.00 g±0.01 g), MP (250 mg±5 mg), and PP (125.0 mg±2.5 mg) were added to a 20 mL glass vial with stirring for about 60 minutes. Added 350 mL SWFI in a 500 mL glass flask and poured the paraben solution into the flask. Rinsed the residual paraben solution remaining in the 20 mL glass vial with portions of SWFI (totaling 100 mL) and transfer rinses to the 500 mL glass flask. (The total volume at this stage is about 90% of the total volume.) The contents were stirred for about 10 minutes. The observed pH was 5.446. The pH was adjusted to 4.192 by adding 1 N HCl. Added a sufficient amount of SWFI with mixing to reach a final volume of 500 mL. Filtered preserved water with 0.2 micron PES filter into glass flask.

Wrapped a 0.8 L wide mouth jug with an amber bag and added 360 mL of preserved water in the jug.

Added Tet HCl (2.00 g±0.04 g), Lido HCl (16.106 g±0.32 g), SMBS (106 mg±2 mg), and Na$_2$EDTA DH (80.0 mg±1.6 mg) powders to the glass jug and stirred for at least about 15 minutes to dissolve contents. Adjusted pH to 3.777 using 1 N HCl. Added Epi HCl (244.0 mg 4.9 mg). Observed pH of 3.774 for LET solution after addition of Epi HCl.

Added HEC 5000 cP (7.04 g 0.14 g) to the jug with vigorous agitation using a mixer (630 rpm) for at least about 60 minutes.

Added a sufficient amount of preserved water to produce final volume of 400 mL with stirring for at least about 15 minutes. Amber colored syringes (e.g., PD syringes, 5 mL each) were filled with 3 mL of LET gels and evaluated for potency, stability, sterility, and endotoxins. Table 8 summarizes the compositional makeup of LET Formulation (Gel) 12.

Preparation of LET Gel 13.

PG (5.00 g±0.01 g), MP (450 mg±9 mg), and PP (50 mg±1 mg) were added to a 20 mL glass vial with stirring for about 60 minutes. Added 350 mL SWFI in a 500 mL glass flask and poured the paraben solution into the flask. Rinsed the residual paraben solution remaining in the 20 mL glass vial with portions of SWFI (totaling 100 mL) and transfer rinses to the 500 mL glass flask. (The total volume at this stage is about 90% of the total volume.) The contents were stirred for about 10 minutes. The observed pH was 5.313. The pH was adjusted to 4.110 by adding 1 N HCl. Added a sufficient amount of SWFI with mixing to reach a final volume of 500 mL. Filtered preserved water with 0.2 micron PES filter into glass flask.

Wrapped a 0.8 L wide mouth jug with an amber bag and added 360 mL of preserved water in the jug.

Added Tet HCl (2.00 g±0.04 g), Lido HCl MH (16.106 g±0.32 g), SMBS (106 mg±2 mg), and Na$_2$EDTA DH (80.0 mg±1.6 mg) powders to the glass jug and stirred for at least about 15 minutes to dissolve contents. Adjusted pH to 3.740 using 1 N HCl. Added Epi HCl (244.0 mg 4.9 mg).

Added sifted HEC (7.04 g±0.14 g) to the jug with vigorous agitation using a mixer (630 rpm) for at least about 60 minutes.

Added a sufficient amount of preserved water to produce final volume of 400 mL with stirring for at least about 15 minutes. Amber colored syringes (e.g., PD syringes, 5 mL each) were filled with 3 mL of LET gels and evaluated for potency, stability, sterility, and endotoxins. Table 8 summarizes the compositional makeup of LET Formulation (Gel) 13.

Preparation of LET Formulation (Gel) 14.

PG (5.00 g±0.01 g) and MP (900 mg±18 mg) were added to a 20 mL glass vial with stirring for about 60 minutes. Added 350 mL SWFI in a 500 mL glass flask and poured the paraben solution into the flask. Rinsed the residual paraben solution remaining in the 20 mL glass vial with portions of SWFI (totaling 100 mL) and transfer rinses to the 500 mL glass flask. (The total volume at this stage is about 90% of the total volume.) The contents were stirred for about 10 minutes. The observed pH was 4.965. The pH was adjusted to 4.160 by adding 1 N HCl. Added a sufficient amount of SWFI with mixing to reach a final volume of 500 mL. Filtered preserved water with 0.2 micron PES filter into glass flask.

Wrapped a 0.8 L wide mouth jug with an amber bag and added 360 mL of preserved water in the jug.

Added Tet HCl (2.00 g±0.04 g), Lido HCl (16.106 g±0.32 g), SMBS (106 mg±2 mg), and $Na_2EDTA$ DH (80.0 mg±1.6 mg) powders to the glass jug and stirred for at least about 15 minutes to dissolve contents. Adjusted pH to 3.774 using 1 N HCl. Added Epi HCl (244.0 mg 4.9 mg).

Added HEC 5000 cP (7.04 g±0.14 g) to the jug with vigorous agitation using a mixer (630 rpm) for at least about 60 minutes.

Added a sufficient amount of preserved water to produce final volume of 400 mL with stirring for at least about 15 minutes. Amber colored syringes (e.g., PD syringes, 5 mL each) were filled with 3 mL of LET gels and evaluated for potency, stability, sterility, and endotoxins. Table 8 summarizes the compositional makeup of LET Formulation (Gel) 14.

TABLE 8

Compositional makeup and Potency Results for LET Formulations (Gels) 12-14.

| | LET Formulations 12-14 | | |
| --- | --- | --- | --- |
| | 12 | 13 | 14 |
| Ingredients | Amount (mg/mL) | | |
| Lido HCl[a] | 40 | 40 | 40 |
| Epi HCl[b] | 0.61 | 0.61 | 0.61 |
| Tet HCl | 5 | 5 | 5 |
| PG | 10 | 10 | 10 |
| SMBS[c] | 0.265 | 0.265 | 0.265 |
| EDTA[e] | 0.2 | 0.2 | 0.2 |
| MP | 0.5 | 0.9 | 1.8 |
| PP | 0.25 | 0.1 | — |
| HEC[f] | 17.6 | 17.6 | 17.6 |
| SWFI | QS | QS | QS |
| pH Adj. | QS to pH 3.92 | QS to pH 3.85 | QS to pH 3.92 |
| Epi. Pot. | 107.1[g] (109.8)[h] | 103.5[g] (111.3)[h] | 110.4[g] (109.5)[h] |
| Lido. Pot. | 100.3[g] (102.7)[h] | 101.1[g] (104.7)[h] | 102.7[g] (101.9)[h] |

TABLE 8-continued

Compositional makeup and Potency Results for LET Formulations (Gels) 12-14.

| | LET Formulations 12-14 | | |
| --- | --- | --- | --- |
| | 12 | 13 | 14 |
| Ingredients | Amount (mg/mL) | | |
| Tet. Pot. | 102.6[g] (96.0)[h] | 105.5[g] (95.8)[h] | 108.0[g] (92.7)[h] |
| MP Pot. | 96.0[g] (97.8)[h] | 97.5[g] (100.3)[h] | 99.8[g] (98.8)[h] |
| PP Pot. | 82.7[g] (Not tested)[h] | 94.8[g] (Not tested)[h] | N/A |
| pH | 3.63[g] (3.55)[h] | 3.61[g] (3.75)[h] | 3.64[g] (3.53)[h] |

Notes:

[a] Lido HCl based on 42.66g/mL Lido HCl MH.

[b] Epi HCl equivalent to 0.51 mg/mL Epi FB.

[c] SMBS ($Na_2S_2O_5$) in an amount of about 0.265 mg/mL corresponds to about 0.0028 mmol of sulfur (viz., 2x(0.265/190.107)).

[e] EDTA based on Na2EDTA DH.

[f] HEC 5000 cP.

[g] Potency- and pH-values evaluated at 235 days after manufacture.

[h] Potency- and pH-values evaluated at 368 days after manufacture.

Room temperature storage of LET Formulations 12-14 showed a substantially unchanged epinephrine content (specification of 90% to 115%) for a period of 368 days. This data readily 5 supports a room temperature shelf-life (e.g., BUD) of about 370 days. (It should be noted that the ratio of mass amount (in mg) of epinephrine free base to the mole amount of sulfur in the sulfite (viz., sodium metabisulfite) is about 183.

As the ready to use LET formulation may be used with an epinephrine content of 90% of the labeled content (e.g., 0.5 mg/mL), an extended shelf-life of 380 days, 390 days, 400 days, and 410 days (or more, e.g., 420 days) may be achieved.

The LET formulations described herein (e.g., LET Formulation (Gel) 14) was further subjected to antimicrobial effectiveness tests ("AET") in accordance with USP<51> and USP<61>.

Briefly, the AET was performed by inoculating samples of each formulation with a high concentration of live organisms ($10^5$-$10^6$ CFU). The samples were mixed thoroughly and placed into 20-25° C. incubation per USP<51>. Two full sets of each formulation were inoculated to evaluate antimicrobial effectiveness at both 14 days (14D) and 28 days (28D) of total incubation time.

At each time point, the samples were removed from incubation and microbial recovery was performed per USP<61> for microbial recovery in the presence of product. Both the log reduction value and log reduction percentage were calculated using the estimated number of organisms in the spiked sample and the number of organisms recovered. Two concentrations of organisms were sampled post-incubation: a high concentration of not more than 1000 CFU per sample (microbicidal), and a lower concentration of not more than 100 CFU per sample (microbiostatic). These concentrations were obtained by serial dilution methods. Tables 9-10 summarize the AET results for LET Formulation (Gel) 14 initially (t=0, Table 9) and after 180-days storage at about 25° C. (Table 10).

TABLE 9

AET for LET Formulation (Gel) 14 (t = 0 d)

| IP | Organism | MIC (CFU) | MCR (CFU) | LRV | LRP | MIC (CFU) | MRA (CFU) | LRV | LRP |
|---|---|---|---|---|---|---|---|---|---|
| 14D | C. albicans | 85 | 0 | N/A | 100% | 854 | 0 | N/A | 100% |
| | A. brasilensis | 89 | 0 | N/A | 100% | 892 | 0 | N/A | 100% |
| | S. aureus | 92 | 0 | N/A | 100% | 916 | 0 | N/A | 100% |
| | P. aerugniosa | 76 | 0 | N/A | 100% | 757 | 0 | N/A | 100% |
| | E. coli | 99 | 0 | N/A | 100% | 991 | 0 | N/A | 100% |
| 28D | C. albicans | 85 | 0 | N/A | 100% | 854 | 0 | N/A | 100% |
| | A. brasilensis | 89 | 0 | N/A | 100% | 892 | 0 | N/A | 100% |
| | S. aureus | 92 | 0 | N/A | 100% | 916 | 0 | N/A | 100% |
| | P. aerugniosa | 76 | 0 | N/A | 100% | 757 | 0 | N/A | 100% |
| | E. coli | 99 | 0 | N/A | 100% | 991 | 0 | N/A | 100% |

Abbreviations: MIC (Microbiostatic Inoculum Concentration), MRC (Microbiostatic Recovery Average), LRV (Log Reduction Value), LRP (Log Reduction Percentage), IP (Incubation period).

TABLE 10

AET for LET Formulation (Gel) 14 (t = 180 d)

| IP | Organism | MIC (CFU) | MCR (CFU) | LRV | LRP | MIC (CFU) | MRA (CFU) | LRV | LRP |
|---|---|---|---|---|---|---|---|---|---|
| 14D | C. albicans | 90 | 0 | N/A | 100% | 899 | 0 | N/A | 100% |
| | A. brasilensis | 96 | 0 | N/A | 100% | 963 | 0 | N/A | 100% |
| | S. aureus | 80 | 0 | N/A | 100% | 801 | 0 | N/A | 100% |
| | P. aerugniosa | 77 | 0 | N/A | 100% | 772 | 0 | N/A | 100% |
| | E. coli | 97 | 0 | N/A | 100% | 967 | 0 | N/A | 100% |
| 28D | C. albicans | 90 | 0 | N/A | 100% | 899 | 0 | N/A | 100% |
| | A. brasilensis | 96 | 0 | N/A | 100% | 963 | 0 | N/A | 100% |
| | S. aureus | 80 | 0 | N/A | 100% | 801 | 0 | N/A | 100% |
| | P. aerugniosa | 77 | 0 | N/A | 100% | 772 | 0 | N/A | 100% |
| | E. coli | 97 | 0 | N/A | 100% | 967 | 0 | N/A | 100% |

Abbreviations: MIC (Microbiostatic Inoculum Concentration), MRC (Microbiostatic Recovery Average), LRV (Log Reduction Value), LRP (Log Reduction Percentage), IP (Incubation period).

To determine if the MP amount of 1.8 mg/mL in LET Formulation (Gel) 14 is effective as an antimicrobial agent, the test results were compared to the acceptance criteria for antimicrobial agents found in Table 3. "Criteria for Tested Microorganisms, Category 2 Products" from USP<51>. As an aside, a "Category 2 Product" is a referred to generally as a topically used product made with an aqueous vehicle. USP<51> specifies that for bacteria the AET results requires not less than 2.0 log reduction from the initial count at 14 days, and no increase from the 14 days count at 28 days. USP<51> also specifies for yeasts and molds that there is no increase from the initial calculated count at 14 and 28 days. When comparing the AET results obtained for LET Formulation (Gel) 14, in view of the guidance from USP<51>, it is plain to see that LET Formulation (Gel) 14 containing MP at 1.8 mg/mL shows a high degree of antimicrobial effectiveness.

Example 7. Preparation of LET Formulations (Gels 15-17 and Solution 18)

Preserved water (500 mL) was prepared similarly as described in Example 6 (e.g., LET Formulation (Gel) 14) for the manufacture of 400 mL LET gel. Table 11 summarizes the compositional makeup of LET Formulations (Gels 15-17 and Solution 18).

TABLE 11

Compositional makeup and AET Results for LET Formulations (Gels 15-17 and Solution 18).

| | LET Formulations 16-18 | | | |
|---|---|---|---|---|
| | 15 | 16 | 17 | 18 |
| Ingredients | Amount (mg/mL) | | | |
| Lido HCl | 40 | 40 | 40 | 40 |
| Epi HCl[a] | 0.61 | 0.61 | 0.61 | 0.61 |
| Tet HCl | 5 | 5 | 5 | 5 |
| PG | 10 | 10 | 10 | 10 |
| SMBS | 0.265 | 0.265 | 0.265 | 0.265 |
| EDTA | 0.2 | 0.2 | 0.2 | 0.2 |
| MP | 0.9 | 1.44 | 1.8 | 1.8 |
| HEC | 17.6 | 17.6 | 35.2 | — |
| SWFI | q.s. | q.s. | q.s. | q.s. |
| pH Adj., QS to pH | 3.770 | 3.680 | 3.769 | 3.779 |
| Batch Size, PW (mL) | 500 | 500 | 500 | 500 |
| Batch Size, Gel/Soln (mL) | 400 | 400 | 400 | 400 |
| AET Results[b] | Pass[c] | Pass[c] | Pass[c] | Pass[c] |

Notes:
[a]Epi HCl equivalent to 0.51 mg/mL Epi FB.
[b]AET results obtained immediately after manufacture.
[c]After 14 day incubation period.

It should be noted that the ratio of mass amount (in mg) of epinephrine free base to the mole amount of sulfur in the sulfite (viz., sodium metabisulfite) is about 183. Potency data (not shown) support a room temperature (e.g., about 22°

C. to about 25° C.) shelf-life stability of at least 380 days (or more), e.g., 420 days (e.g., LET Formulations 15-16).

Example 8. Preparation of LET Formulations (Gels 19-22 and Solutions 23-24)

Preserved water (500 mL) was prepared similarly as described in Example 6 (e.g., LET Formulation (Gel) 14) for the manufacture of 400 mL LET gel. Table 12 summarizes the compositional makeup of LET Formulations (Gels 19-22 and Solutions 23-24).

TABLE 12

Compositional makeup and Potency Results for LET Formulations (Gels 19-22 and Solutions 23-24).

| Ingredients | LET Formulations 19-24 | | | | | |
|---|---|---|---|---|---|---|
| | 19 | 20 | 21 | 22 | 23 | 24 |
| | Amounts (mg/mL) | | | | | |
| Lido HCl | 40 | 40 | 40 | 40 | 40 | 40 |
| Epi HCl | 0.61 | 0.61 | 0.61 | 0.61 | 0.61 | 0.61 |
| Tet HCl | 5 | 5 | 5 | 5 | 5 | 5 |
| PG | 10 | 10 | 10 | 10 | 10 | 10 |
| SMBS | 0.265 | 0.265 | 0.265 | 0.265 | 0.265 | 0.265 |
| $Na_2$EDTA DH | 0.2 | 0.2 | 0.2 | 0.2 | 0.2 | 0.2 |
| MP | 1.8 | 1.8 | 1.8 | 1.8 | 1.8 | 1.8 |
| HEC | 17.6 | 17.6 | 35.2 | 35.2 | — | — |
| SWFI | QS | QS | QS | QS | QS | QS |
| pH Adj., QS to pH | 3.758 | 3.754 | 3.752 | 3.717 | 3.767 | 3.750 |
| Epi Pot [a] | 109.3 | 108.8 | 111.9 | 112.9 | 109.0 | 107.4 |
| Lido Pot.[a] | 99.5 | 98.5 | 109.7 | 110.3 | 106.4 | 104.4 |
| Tet. Pot.[a] | 104.9 | 103.9 | 107.7 | 107.8 | 105.3 | 103.3 |
| MP Pot.[a] | 95.8 | 95.6 | 100.4 | 102.4 | 100.0 | 96.1 |
| pH[a] | 3.64 | 3.58 | 3.69 | 3.67 | 3.49 | 3.48 |
| USP <61>[b] | Pass (258 d) | — | — | Pass (199 d) | — | Pass (202 d) |
| USP <62>[c] | Pass (257 d) | — | — | Pass (200 d) | — | Pass (203 d) |

[a] Potency-and pH-values evaluated at 370 days after manufacture.
[b] USP <61>-Test for Total Aerobic Microbial (<10 CFU/mL).
[c] USP <62>-Test for *Pseudomonas aeruginosa* and *Staphylococcus aureus*.

It should be noted that the ratio of mass amount (in mg) of epinephrine free base to the mole amount of sulfur in the sulfite (viz., sodium metabisulfite) is about 183. The potency results of LET Formulations 19-24 support a room temperature (e.g., 22-25° C.) shelf-life stability (e.g., BUD) of at least 370 days.

Practical Utility

The pharmaceutical formulations (e.g., LET formulations) disclosed herein exhibit improved properties relative to previous LET topical products, including long-term stability at room temperature, confirmed antimicrobial efficacy, and a clinical benefit.

For instance, the LET formulations exhibit an epinephrine stability that is substantially improved compared to previous LET preparations. See e.g., USP43's LET gel and Nationwide Children's LET II 3ML. The added stability is particularly surprising since no efforts were made to exclude oxygen and since epinephrine is known to degrade in the presence of oxygen. See e.g., Connors at 440. With the understanding that the LET formulations may further comprise up to 40 mg/L of oxygen, the stabilities observed herein are especially surprising since the molar ratio of epinephrine to oxygen ($O_2$) is about 1.25 and the molar ratio of oxygen ($O_2$) to sulfite (e.g., metabisulfite) is about 1.

Further, the LET formulations disclosed herein have a beyond-use date (BUD) of at least 8 months or more (e.g., 365 days or more) when stored at room temperature (e.g., 22-25° C.). The ready to use LET formulations disclosed herein exhibit substantially improved handling and/or storage properties compared to other products, for example, USP43's LET (4%/0.05%/1%) gel, BUD of 60 days stored at room temperature);

QuVa's LET (4%/0.05%/0.5%) gel, BUD 90 days at room temperature);

Nationwide Children's LET II 3ML (4%/0.05%/0.5%) gel, BUD 150 days refrigerated (21-days room temperature);

Edge Pharma's LET (4%/0.05%/0.5%) gel, BUD 150 days refrigerated);

Fagron's LET (4%/0.18%/0.5%) gel, BUD of 90 days); and

Fagron's LETS GEL KIT™ (4%/0.18%/0.5%) gel with BUD of 90 days).

The ready to use LET formulations disclosed herein include a preservative that inhibits all microbial growth for the stated storage period.

As stated above, the ratio of mass amount (in mg) of epinephrine free base to the mole amount of sulfur in the sulfite (viz., sodium bisulfite) is 29 for the USP 43 topical gel with a BUD 60 days at room temperature.

It is remarkable a ratio of mass amount (in mg) of epinephrine free base to the mole amount of sulfur in the sulfite (in mmol) of from 175 to 185 (e.g., about 183) results in an improved BUD of 240 days or more (e.g., 360-420 days) for the LET formulations disclosed herein.

Syringe products comprising the LET formulations disclosed herein are ready to use and offer a clinical advantage of having a pH that affords less discomfort when applied to a laceration of a patient in need of an anesthetic effect.

Aspects

Aspect 1. A pharmaceutical formulation, comprising: lidocaine or a pharmaceutically acceptable salt thereof, in an amount of about 30 mg/mL to about 50 mg/mL based on lidocaine free base; epinephrine or a pharmaceutically acceptable salt thereof, in an amount of about 0.25 mg/mL to about 2.5 mg/mL based on epinephrine free base; tetracaine or a pharmaceutically acceptable salt thereof, in amount of about 3 mg/mL to about 10 mg/mL based on tetracaine free base; a sulfite comprising metabisulfite ($S_2O_5^{2-}$), bisulfite ($HSO_3^-$), or a combination thereof; a chelating agent in an amount of from about 0.1 mg/mL to about 1 mg/mL; an antimicrobial effective amount of a preservative; optionally, a glycol, in an amount of about 1 mg/mL to about 20 mg/mL; optionally, a pharmaceutically acceptable buffer; optionally, a sufficient amount of a gelling agent; and a sufficient amount of water; wherein the formulation has a pH of from about 3.6 to about 4.2; and wherein the formulation has a ratio of the mass amount (in mg) of epinephrine free base to the mole amount of sulfur in the sulfite (in mmol) that ranges from 179 to 185.

Aspect 2. The pharmaceutical formulation of Aspect 1, wherein the formulation comprises about 40 mg/mL lidocaine hydrochloride and about 5 mg/mL tetracaine hydrochloride.

Aspect 3. The pharmaceutical formulation of any one of Aspects 1-2, wherein the formulation comprises about 0.25 mg/mL L-epinephrine free base.

Aspect 4. The pharmaceutical formulation of any one of Aspects 1-3, wherein the formulation comprises from about 0.5 mg/mL to about 1 mg/mL epinephrine free base.

Aspect 5. The pharmaceutical formulation of any one of Aspects 1-4, wherein the sulfite comprises sodium metabisulfite in an amount that is about 0.52 times the mass amount of epinephrine free base.

Aspect 6. The pharmaceutical formulation of any one of Aspects 1-6, wherein the sulfite comprises sodium bisulfite in an amount that is about 0.57 times the mass amount of epinephrine free base.

Aspect 7. The pharmaceutical formulation of any one of Aspects 1-6, wherein the chelating agent comprises a disodium salt of ethylenediaminetetraacetic acid in an amount of from about 0.1 mg/mL to about 1 mg/mL.

Aspect 8. The pharmaceutical formulation of any one of Aspects 1-7, wherein the chelating agent comprises a disodium salt of ethylenediaminetetraacetic acid in an amount of about 0.2 mg/mL.

Aspect 9. The pharmaceutical formulation of any one of Aspects 1-8, wherein the preservative comprises at least one of methylparaben, propylparaben, or a pharmaceutically acceptable salt thereof.

Aspect 10. The pharmaceutical formulation of any one of Aspects 1-9, wherein the preservative comprises at least one of methylparaben, propylparaben, or a pharmaceutically acceptable salt thereof.

Aspect 11. The pharmaceutical formulation of any one of Aspects 1-10, wherein the preservative comprises at least one of methylparaben, propylparaben, or a pharmaceutically acceptable salt thereof, in an amount of from about 0.1 mg/mL to about 2 mg/mL.

Aspect 12. The pharmaceutical formulation of any one of Aspects 1-11, comprising a glycol in an amount of from about 1 mg/mL to about 20 mg/mL.

Aspect 13. The pharmaceutical formulation of any one of Aspects 1-12, comprising a pharmaceutically acceptable buffer.

Aspect 14. The pharmaceutical formulation of any one of Aspects 1-13, comprising a pharmaceutically acceptable buffer in an amount of from about 1 mM to about 10 mM.

Aspect 15. The pharmaceutical formulation of any one of Aspects 1-14, comprising a sufficient amount of a gelling agent in an amount of from about 0.1% to about 50%.

Aspect 16. The pharmaceutical formulation of any one of Aspects 1-5 and 7-15, comprising: a) lidocaine hydrochloride in an amount of about 40 mg/mL; b) racepinephrine hydrochloride in an amount of about 0.61 mg/mL; c) tetracaine hydrochloride in an amount of about 5 mg/mL; d) propylene glycol in an amount of about 10 mg/mL; e) sodium metabisulfite in an amount of about 0.27 mg/mL; f) a disodium salt of ethylenediaminetetraacetic acid in an amount of about 0.2 mg/mL; g) a paraben comprising methylparaben in an amount of from about 0.9 mg/mL to about 1.8 mg/mL; h) a gelling agent comprising hydroxyethylcellulose in an amount of from 0 mg/mL to about 40 mg/mL; and i) a sufficient amount of water; wherein the pharmaceutical formulation has a pH of from about 3.6 to about 4.2.

Aspect 17. The pharmaceutical formulation of any one of Aspects 1-4 and 6-15, comprising: a) lidocaine hydrochloride in an amount of about 40 mg/mL; b) racepinephrine hydrochloride in an amount of about 0.61 mg/mL; c) tetracaine hydrochloride in an amount of about 5 mg/mL; d) propylene glycol in an amount of about 10 mg/mL; e) sodium bisulfite in an amount of about 0.29 mg/mL; f) a disodium salt of ethylenediaminetetraacetic acid in an amount of about 0.2 mg/mL; g) a paraben comprising methylparaben in an amount of from about 0.9 mg/mL to about 1.8 mg/mL; h) a gelling agent comprising hydroxyethylcellulose in an amount of from 0 mg/mL to about 40 mg/mL; and i) a sufficient amount of water; wherein the pharmaceutical formulation has a pH of from about 3.6 to about 4.2.

Aspect 18. A syringe product comprising the pharmaceutical formulation of any one of Aspects 1-17.

Aspect 19. A method for providing procedural analgesia to a patient in need thereof, which comprises topically administering the pharmaceutical formulation of any one of Aspects 1-18 to the patient in need of analgesia.

Aspect 20. A process for preparing the pharmaceutical formulation of any one of Aspects 1-18, which comprises: a) dissolving the preservative in a vehicle comprising water for injection, a glycol, or a combination thereof to obtain a preservative solution; b) dissolving the preservative solution in water for injection to obtain a preserved water solution; c) dissolving in the preserved water solution: (i) lidocaine or a pharmaceutically acceptable salt thereof; (ii) tetracaine or a pharmaceutically acceptable salt thereof, (iii) to sulfite; (iv) the chelating agent; and optionally, (v) the pharmaceutically acceptable buffer; d) optionally, adjusting the pH of the step c) solution to a pH of from about 3.6 to about 4.2; e) dissolving epinephrine or a pharmaceutically acceptable salt thereof in the step c) solution or the step d) solution; f) optionally, adjusting the pH of the step e) solution to a pH of from about 3.6 to about 4.2; and g) optionally adding the gelling agent to the step e) solution or the step f) solution.

CITED INFORMATION

Berge et al., Pharmaceutical Salts, Journal of Pharmaceutical Sciences (1977) 66(1), 1-19 ("Berge").

Bernards et al., *Effect of Epinephrine on Lidocaine Clearance In Vivo*, Anesthesiology (1999) 91(4): 962-968 ("Bernards").

Connick et al., *Equilibrium Constant for the Dimerization of Bisulfite Ion to Form $S_2O_5^{2-}$*, Inorganic Chemistry (1982) 21(1): 103-107 ("Connick").

Connors et al., *Chemical Stability of Pharmaceuticals: A Handbook for Pharmacists*, $2^{nd}$ Ed. (1986), pp. 438-448 ("Connors").

Edge Pharma's LET (5%/0.05%/0.5%) Gel Topical Anesthetic, see edgepharma.com/products/nonsterile-products/, last accessed on Feb. 26, 2021.

Ernst et al. *LAT (Lidocaine-Adrenaline-Tetracaine) Versus TAC (Tetracaine-Adrenaline-Cocaine)for Topical Anesthesia in Face and Scalp Lacerations*, American Journal of Emergency Medicine (1995) 13(2): 151-154 ("Ernst 1995").

Fagron's LETS GEL KIT™ Convenience Pack (4%/0.1%/0.5%), us.fagron.com/sites/default/files/wysiwyg/faus_letsgelkit_instructions_0118_vfinal.pdf, last accessed on Feb. 26, 2021.

*Fagron Inc. Issues Voluntary Nationwide Recall of LETS GEL KIT Convenience Packs Due to Potential Microbial Contamination of Non-Sterile Products*, FDA Publish Date of Nov. 1, 2019, www.fda.gov/safety/recalls-market-withdrawals-safety-alerts/fagron-inc-issues-voluntary-nationwide-recall-lets-gel-kit-convenience-packs-due-potential-microbial, last accessed on Mar. 1, 2021 ("LETS GEL KIT™ Product Recall Notice").

Fagron's LET Sterile Topical Gel, www.fagronsterile.com/let-gel, last accessed on Mar. 2, 2021.

Flynn, G. L., Buffers-pH Control within Pharmaceutical Systems, Journal of the Parenteral Drug Association (1980) 34(2) 139-162 ("Flynn").

Grubstein et al., *Stabilization of Epinephrine in a Local Anesthetic Injectable Solution using Reduced Levels of Sodium Metabisulfite and EDTA*, Drug Dev. Ind. Pharm. (1992) 18(14): 1549-1566.

Handbook of Pharmaceutical Excipients, 6th Ed., Eds. Rowe et al. (2009), pages 181-183 247-250, 311-324, 438-441, 506-509 ("Handbook").

Kundu et al., *Principles of Office Anesthesia: Part II Topical Anesthesia*, Am. Fam. Physician (2002) 66(1): 99-102 ("Kundu").

Larson et al., *Stability of epinephrine hydrochloride in an extemporaneously compounded topical anesthetic solution of lidocaine, racepinephrine, and tetracaine*, American Journal Health-System Pharmacy (1996) 53(6): 659-662 ("Larson").

Lidocaine Jelly, Prescribing Information, as of Oct. 1, 2020.

The Merck Index: An Encyclopedia of Chemicals, Drugs, and Biologicals, $14^{th}$ Edition (2006), pages 3619, 5480, and 9191 ("Merck Index").

Nationwide Children's compounding report dated Mar. 23, 2010 related to LET II 3ML Topical Gel, www.nationwidechildrens.org/-/media/nch/specialties/pharmacy/compounding-formulas/let-gel.ashx, last accessed on Mar. 2, 2021.

Resch et al., *Topical Anesthesia for Pediatric Lacerations: A Randomized Trial of Lidocaine-Epinephrine-Tetracaine Solution Versus Gel*, Annals of Emergency Medicine (1998) 32(6): 693-697 ("Resch").

Sabatier et al., *Simultaneous HPLC determination of lidocaine-epinephrine-tetracaine in a topical solution for pediatric anesthesia*, Journal of Pharmacy Research (2016) 10(11): 692-695 ("Sabatier").

Sherman et al., *Let Us Use LET. A Quality Improvement Initiative*, Pediatric Emergency Care (2016) 32(7): 440-443 ("Sherman").

Singer et al., *LET versus EMLA for Pretreating Lacerations: A Randomized Trial*, Academic Emergency Medicine (2001) 8(3): 223-230 ("Singer").

U.S. Pat. No. 5,585,398 A, Topical Anesthetic comprising Lidocaine, Adrenaline, and Tetracaine, and its Method of Use, issued on Dec. 17, 1996, to Amy A. Ernst ("Ernst 1996").

U.S. Pat. No. 6,708,822 B1, Compositions and Kits for Compounding Pharmaceuticals, issued on Mar. 23, 2004 to Indu A. Muni of CutisPharma, Inc. ("Muni").

U.S. Pat. No. 8,628,805 B2, Stabilized Composition comprising at least one Adrenergic Compound, issued on Jan. 14, 2014, to Baillie et al. of Alk AG ("Baillie").

U.S. Pat. No. 10,952,962 B1, Ready to use liquidformulation, issued on Mar. 23, 2021, to Leeah et al. of QuVa Pharma, Inc ("Leeah").

U.S. Pat. No. 10,952,963 B2, Ready to use liquid RECK-formulation, issued on Mar. 23, 2021, to Leeah et al. of QuVa Pharma, Inc.

U.S. Patent Application Publication No. US 2021/0251888 A1, Ready to use liquid formulation, published on Aug. 19, 2021 to Leeah et al. of QuVa Pharma, Inc.

U.S. Pharmacopeia 28, (2005), pages 3-12 and 2457-2460 ("USP 28").

U.S. Pharmacopeia 43 | National Formulary 38, Lidocaine, Racepinephrine, and Tetracaine Hydrochlorides Compounded Topical Gel, (2020), pages 3—("USP 43").

Zanon et al., *Stability of a novel Lidocaine, Adrenaline and Tetracaine sterile thermosensitive gel: A ready-to-use formulation*, European Journal Pharmaceutical Sciences (2019) 136: 104962 (1-6), DOI: 10.1016/j.ejps.2019.104962 ("Zanon").

This application claims priority to U.S. Provisional Patent Application No. 63/162,593, filed on Mar. 18, 2021.

Information cited herein is incorporated by reference in its entirety, including U.S. Provisional Patent Application No. 63/162,593. If information incorporated by reference conflicts with the meaning of a term or an expression disclosed herein, the meaning of the term or the expression disclosed herein controls.

The invention claimed is:

1. A ready-to-use pharmaceutical formulation, consisting of:
   a) lidocaine hydrochloride in an amount of 40 mg/mL;
   b) epinephrine hydrochloride in an amount of 0.61 mg/mL;
   c) tetracaine hydrochloride in an amount of 5 mg/mL;
   d) propylene glycol in an amount of 10 mg/mL;
   e) sodium metabisulfite in an amount of 0.265 mg/mL;
   f) a disodium salt of ethylenediaminetetraacetic acid dihydrate ($Na_2$EDTA DH) in an amount of 0.2 mg/mL;
   g) methylparaben in an amount of 1.8 mg/mL;
   h) hydroxyethylcellulose in an amount of 0 mg/mL, 17.6 mg/mL, or 35.2 ma/mL; and
   i) a sufficient amount of sterile water for injection;
   wherein the ready-to-use pharmaceutical formulation has a pH of from 3.6 to 3.9; and
   wherein the ready-to-use pharmaceutical formulation has epinephrine hydrochloride content of 90% to 115% of the epinephrine hydrochloride content of 0.61 mg/mL after storage at a temperature ranging from 22° C. to 25° C. for 380 days.

2. A method for providing procedural analgesia to a patient in need thereof, which comprises topically administering an effective amount of the ready-to-use pharmaceutical formulation of claim 1 to the patient in need of analgesia.

3. A process for preparing the ready-to-use pharmaceutical formulation of claim 1, which comprises:
  a) dissolving methylparaben in propylene glycol to obtain a preservative solution;
  b) dissolving the preservative solution in water for injection to obtain a preserved water solution;
  c) dissolving in the preserved water solution: (i) the lidocaine hydrochloride; (ii) the tetracaine hydrochloride; (iii) the sodium metabisulfite; and (iv) the $Na_2EDTA$ DH;
  d) optionally, adjusting the pH of the step c) solution to a pH of from 3.6 to 3.9;
  e) dissolving the epinephrine hydrochloride in the step c) solution or the step d) solution;
  f) optionally, adjusting the pH of the step e) solution to a pH of from 3.6 to 3.9;
  g) filtering the solution of step e) or the solution of step f) using a 0.2 micron polyethersulfone filter; and
  h) optionally adding the hydroxyethylcellulose to the step g) solution.

4. The ready-to-use pharmaceutical formulation of claim 1, wherein the pharmaceutical formulation contains 0 mg/mL of hydroxyethylcellulose.

5. The ready-to-use pharmaceutical formulation of claim 1, wherein the hydroxyethylcellulose is present in an amount of 17.6 mg/mL.

6. The ready-to-use pharmaceutical formulation of claim 1, wherein hydroxyethylcellulose is present in an amount of about 35.2 mg/mL.

7. The ready-to-use pharmaceutical formulation of claim 1, wherein the pharmaceutical formulation has a pH of from 3.6 to 3.8.

8. The ready-to-use pharmaceutical formulation of claim 1, wherein the formulation is contained in an amber-colored syringe.

* * * * *